United States Patent
Tokutake et al.

(10) Patent No.: US 7,079,759 B2
(45) Date of Patent: Jul. 18, 2006

(54) SATURATED STEAM GENERATOR, STEAM STERILIZER, AND STEAM STERILIZATION METHOD

(75) Inventors: Kouichi Tokutake, Koushoku (JP); Takami Miyasaka, Koushoku (JP); Takashi Kugue, Toyama (JP)

(73) Assignee: Sakura Seiki Co., Ltd., Nagano (JP)

(*) Notice: Subject to any disclaimer, the term of this patent is extended or adjusted under 35 U.S.C. 154(b) by 271 days.

(21) Appl. No.: 10/332,482

(22) PCT Filed: Jul. 10, 2001

(86) PCT No.: PCT/JP01/05991

§ 371 (c)(1),
(2), (4) Date: Jan. 9, 2003

(87) PCT Pub. No.: WO02/04860

PCT Pub. Date: Jan. 17, 2002

(65) Prior Publication Data

US 2003/0145806 A1 Aug. 7, 2003

(30) Foreign Application Priority Data

Jul. 11, 2000  (JP) .......................................... 2000-21413
Jul. 11, 2000  (JP) ........................................ 2000-210421

(51) Int. Cl.
*B01D 1/00* (2006.01)

(52) U.S. Cl. ...................................... 392/394; 239/135
(58) Field of Classification Search ................. 392/386, 392/387, 394, 396, 397, 398, 400, 401, 402; 422/25, 26, 295, 298, 299; 239/135, 136
See application file for complete search history.

(56) References Cited

U.S. PATENT DOCUMENTS 2,302,528 A * 11/1942 Conklin ..................... 236/44 A
2,883,511 A *  4/1959 Gooldy ........................ 239/136
4,808,377 A *  2/1989 Childers et al. ............... 422/26

FOREIGN PATENT DOCUMENTS

| JP | 1-274764 | 11/1989 |
| JP | 3-86168 | 4/1991 |
| JP | 4-189361 | 7/1992 |
| JP | 9-206359 | 8/1997 |
| JP | 09-285527 | 11/1997 |
| JP | 2000-65302 | 3/2000 |
| JP | 2000-97498 | 4/2000 |
| JP | 2000-161786 | 6/2000 |

* cited by examiner

*Primary Examiner*—Sang Paik
(74) *Attorney, Agent, or Firm*—Jordan and Hamburg, LLP

(57) ABSTRACT

A saturated steam generator which is provided with a heat source for heating water to generate saturated steam and which can be small-sized. A saturated steam generator for generating saturated steam by heating water with superheated steam resulting from being superheated in a heat transmission tube (16) inserted into a heat storage tank (10), characterized by the provision of a saturated steam generator tank (12), wherein in the heat storage tank (10), disposed in a heat storage section composed by having a solid heat storage material and a liquid heat storage material filled therein are a heat transmission tube (16) and a heater (44), which heats the solid heat storage material and the liquid heat storage material, it being arranged that superheated steam resulting from passing through the heat transmission tube (16) is used as a heat source to heat stored water (22) so as to generate saturated steam.

22 Claims, 10 Drawing Sheets

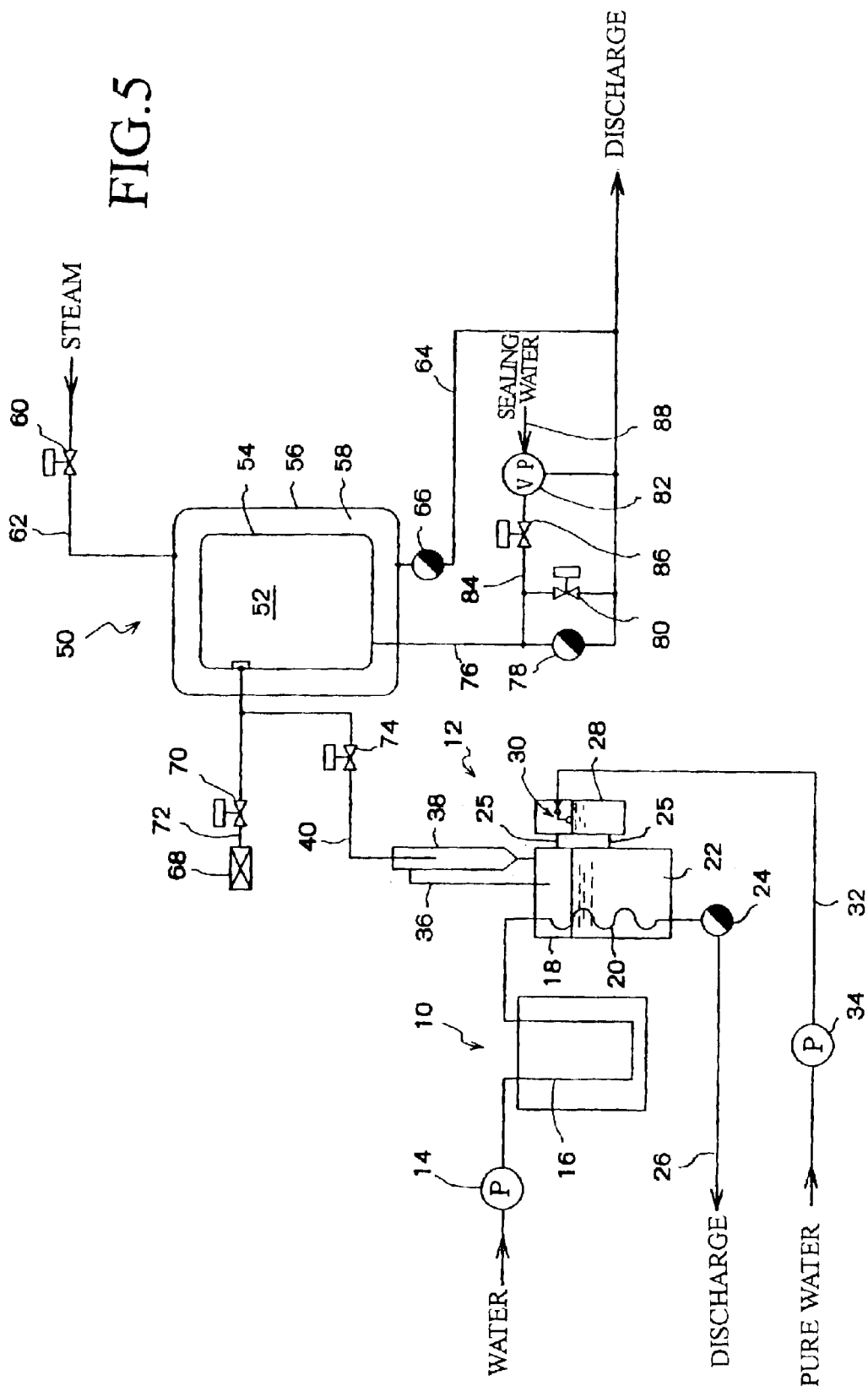

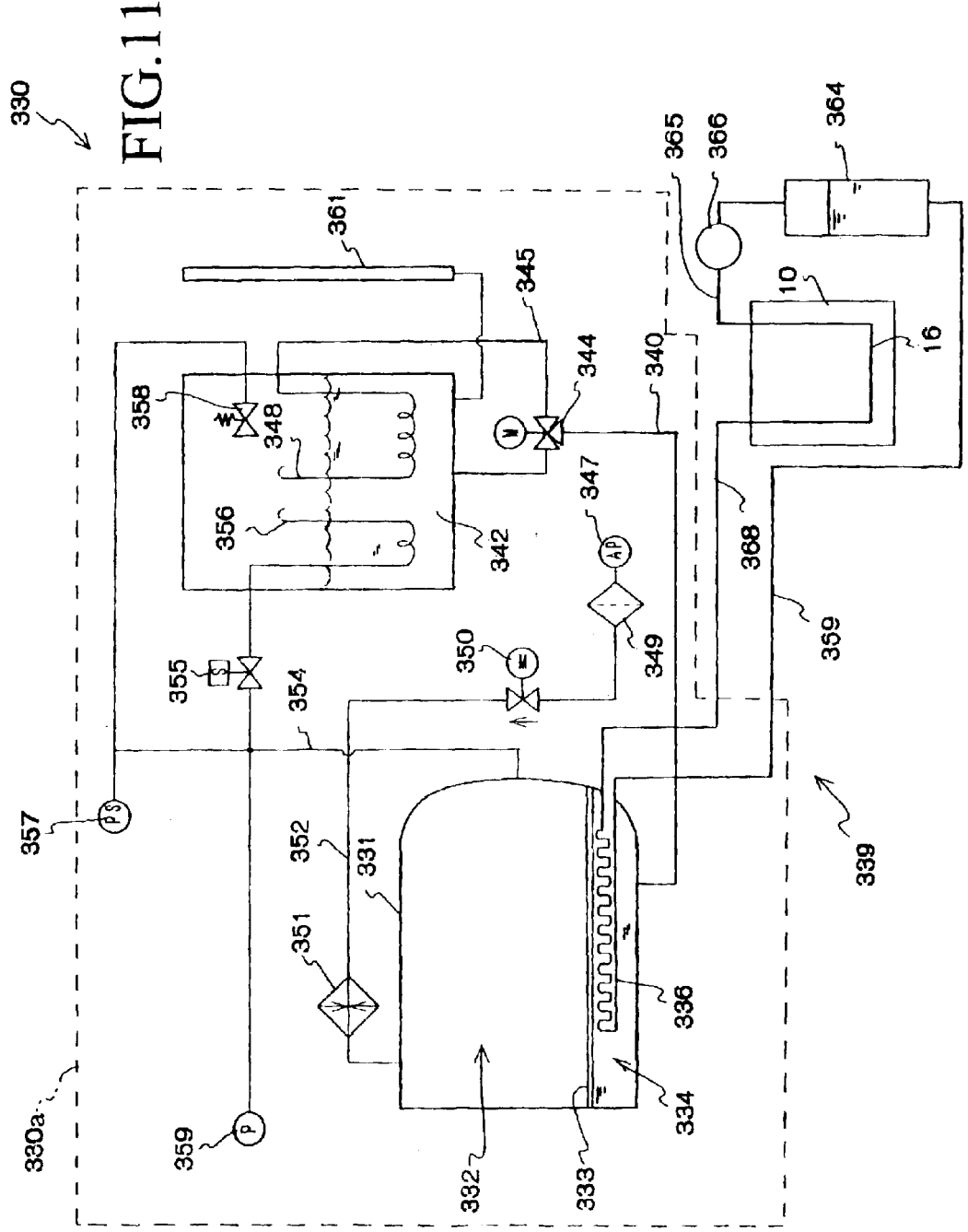

SATURATED STEAM GENERATOR, STEAM STERILIZER, AND STEAM STERILIZATION METHOD

FIELD OF TECHNOLOGY

The present invention relates to a saturated steam generator, a steam sterilizer and a steam sterilization method.

BACKGROUND TECHNOLOGY

Conventionally, in hospitals, etc., articles to be sterilized, e.g., bandages, surgical knives, forcipes, operating gowns, are usually sterilized by a sterilization method comprising the steps of: accommodating the articles in a sterilizing chamber of a sterilizer; pressurizing the sterilizing chamber by saturated steam until reaching prescribed pressure; and maintaining the pressure and temperature in the sterilizing chamber for a prescribed time.

In the case of a large-sized sterilizer capable of sterilizing a large amount of articles, saturated steam is supplied to the sterilizer from a large boiler of a hospital.

If the saturated steam supplied from the large boiler is improper for sterilization or if required capacity of saturated steam for a plurality of sterilizers is greater than capacity of the boiler, a saturated steam generator must be provided to each sterilizer.

For example, a steam sterilizer having a saturated steam generator is disclosed in Japanese Patent Gazette No. 9-285527, wherein saturated steam (pure saturated steam) generated by evaporating pure water, which has been precise-filtered or deionization-treated, is supplied into a sterilizing chamber.

The steam sterilizer disclosed in the Japanese gazette is shown in FIG. 13. In FIG. 13, a body proper 100 of the steam sterilizer comprises: an inner cylinder 104 in which a sterilizing chamber 102 for accommodating articles to be sterilized is formed; an outer cylinder 106 provided outside of the inner cylinder 104; and a jacket 108 provided between the inner cylinder 104 and the outer cylinder 106.

The steam sterilizer shown in FIG. 13 has a steam generator 110 in which pure water supplied by a water supply tube is evaporated to generate pure steam. In the steam generator 110, steam, which is used as a heat source for evaporating pure water, is generated by a large boiler, so it is supplied via a steam tube 120, a control valve 118, a jacket 108 of the steam sterilizer, and a tube 119. The steam supplied to the jacket 108 is used for heating the inner cylinder 104.

The pure steam generated by the steam generator 110 is directly supplied to the sterilizing chamber 102 of the body proper 100 via a pure steam supply tube 116, in which a control valve 114 is provided to a mid part.

The pure steam, which has sterilized the articles in the sterilizing chamber 102, is discharged via a discharge tube 122 and a tube 124, to which a control valve 126 is provided. When pressure in the sterilizing chamber 102 falls to the atmospheric pressure, the control valves 114 and 126 are closed, a water ring vacuum pump 130 is actuated, a control valve 128 of a vacuum tube 132 is opened, so that a vacuum condition is produced in the sterilizing chamber 102. The vacuum condition is produced to dry the articles, on which condensed water of the pure seam is stuck.

When the pressure of the sterilizing chamber 102 is increased to the atmospheric pressure and the sterilized articles are taken out therefrom, clean air is introduced into the sterilizing chamber 102 via a filter 134 and a tube, to which a control valve 136 is provided.

Note that, a part of sealing water of the vacuum pump 130 is lost due to evaporation caused by sucking the pure steam, but the loss is supplemented by supplying water via a tube 131.

The steam sterilizer shown in FIG. 13 employs the pure steam, which is generated by evaporating pure water, as steam for sterilization. Namely, saturated steam, which is generated in a large boiler by heating water including a water conditioning agent, is not used for sterilization, so that no water conditioning agent is stuck onto the sterilized articles.

The steps of the sterilization in the sterilizing chamber 102 of the steam sterilizer shown in FIG. 13 are shown in FIG. 14. FIG. 14 shows variation of inner pressure in the sterilizing chamber 102 with respect to time elapsed, and the steps of the steam sterilization are a conditioning step, a sterilization step, a discharge step, a dry step and a final step.

Firstly, the conditioning step is started after the sterilizing chamber 102, in which the articles to be sterilized have been accommodated, is air-tightly closed. After the vacuum pump 130 is actuated and the control valve 128 is opened so as to discharge air in the sterilizing chamber 102 and produce the vacuum condition therein, the conditioning step alternately repeats two actions: a heating action, in which the control valve 114 of the tube 116 is opened to heat the articles accommodated in the sterilizing chamber 102; and a pressure reducing action, in which the vacuum pump 130 is actuated and the control valve 128 is opened to discharge air and steam from the sterilizing chamber 102 and reduce pressure therein. The conditioning step is executed so as to securely discharge air in the articles and rise inner temperature of the articles as well as surface temperature thereof when the steam is supplied into the sterilizing chamber 102 to heat the articles.

After the articles are fully heated in the conditioning step, the control valve 114 is opened to supply saturated steam into the sterilizing chamber 102 until reaching prescribed pressure, then the pressure and temperature in the sterilizing chamber 102 are maintained for a prescribed time. With this action, bacilli stuck on the articles accommodated in the sterilizing chamber 102 can be sterilized.

Then, the pressurizing steam in the sterilizing chamber 102 is discharged by opening the control valve 126, and the dry step, in which the articles wetted in the sterilization step wilt be dried, is started.

In the dry step, the pressurizing steam has been discharged from the sterilizing chamber 102 and the pressure therein has been reduces to the atmospheric pressure, then the inner pressure of the sterilizing chamber 102 is further reduced by opening the control valve 128 (closing the control valve 126) and actuating the vacuum pump 130 so as to evaporate water stuck on the sterilized articles.

By evaporating water included in the articles, the temperature of the articles fall, so that amount of evaporation from the articles is reduced.

Therefore, the control valve 136 is opened to introduce heated clean air into the sterilizing chamber 102 so as to increase the inner pressure of the sterilizing chamber 102 to near the atmospheric pressure and rise the temperature therein, so that the water stuck on the sterilized articles can be easily evaporated. Further, the inner pressure of the sterilizing chamber 102 is reduced again so as to evaporate the water left in the heated articles.

The heating action and the pressure reducing action are alternately repeated a plurality of times so as to fully dry the articles. The reason of repeating the actions is that bacilli in the air stick onto and proliferate on the articles if the articles not sufficiently dried are taken out from the sterilizing chamber 102.

After the dry step is completed, clean air is introduced into the sterilizing chamber 102 by opening the control valve 136.

Note that, the steam is supplied to the jacket 108 during the steps via the tube 120 and the control valve 118, so that the sterilizing chamber 102 is always heated.

The steam sterilizer shown in FIG. 13 is capable of sterilizing and drying the articles.

However, in the steam sterilizer shown in FIG. 13, the steam generator 110 for evaporating pure water must be provided, and the steam generator 110 is large-sized, so that the steam generator shown in FIG. 3 must be large-sized.

Since the saturated steam, which has passed through the jacket 108 and whose temperature has fallen, is used as a heat source of the steam generator 110, satisfied temperature difference between the saturated steam as the heat source and the pure steam cannot be made. Thus, heat conduction area of the heater of the steam generator 110 must broad, so that the steam generator 110 must be large-sized.

On the other hand, if superheated steam is generated in a large boiler so as to use as the heat source of the steam generator 110, the temperature difference between the saturated steam as the heat source and the pure steam can be greater, but generating the superheated steam is not improper for the boiler because thermal efficiency of the boiler is made lower.

Further, in the case of using the superheated steam generated by the large boiler as the heat source of the steam generator 110, the steam generator 110 depends on the boiler, so load of the boiler cannot be reduced, on the contrary load of the boiler is increased.

Generally, in the dry step, heated clean air is introduced into the sterilizing chamber so as to heat the articles, whose temperature has been fallen due to evaporation under negative pressure atmosphere. Thus, clean air must be heated, a tube 138 for introducing clean air into the sterilizing chamber is wound on an outer circumferential face of the outer cylinder 106, which is heated by saturated steam supplied to the jacket 108.

However, heat conductivity of air is quite lower than that of water, so winding length of the tube 138 must be long so as to heat air until reaching prescribed temperature.

On the other hand, if the winding length of the tube 138 is long, flow resistance of air in the tube 138 is made greater, so that it is difficult to introduce prescribed amount of air into the sterilizing chamber in a short time; therefore an inner diameter of the tube 138 must be greater.

By using the heated air to heat the articles whose temperature has been fallen by evaporating water under negative pressure atmosphere in the dry step, the steam sterilizer must be complex and large-sized.

A first object of the present invention is to provide a small-sized saturated steam generator including a heat source capable of heating and evaporating stored water.

A second object of the present invention is to provide a steam sterilizer having a small-sized saturated steam generator including a heat source capable of heating and evaporating stored water.

A third object of the present invention is to provide a steam sterilizer and a steam sterilization method capable of drying an article to be sterilized in a dry step, in which the article, which has been wetted in a sterilization step, without using heated air.

In some small steam sterilizers, e.g., a desk steam sterilizer used in a laboratory or a clinic, a saturated steam generator is provided in a sterilizing chamber which acts as a pressure vessel. In such steam sterilizer, a lower part of a vessel section of the sterilizing chamber is formed as a water stering section, and steam is directly generated in the sterilizing chamber.

An example of the conventional desk steam sterilizer is shown in FIG. 15. In the desk steam sterilizer 200 shown in FIG. 15, a sterilizing chamber 212, in which articles to be sterilized are accommodated, is provided in a vessel section 211, which acts as a pressure vessel. A mount plate 213, on which the articles will be mounted, is provided in the vessel section 213, and a part of the vessel section 211 above the mount plate 213 is the sterilizing chamber 212. A part of the vessel section 211 under the mount plate 213 is a water storing section 214.

A heater 216 for heating water is provided in the water storing section 214. The heater 216 is an electric heater.

In the desk steam sterilizer 200, the heater 216 heats and evaporates water in the water storing section 214, so that the articles can be sterilized by steam, which is filled in the vessel section 211 and whose temperature, humidity and pressure are prescribed values.

Usually, electric heaters are used as heaters for heating water and air. Therefore, electric power must be applied to the heater during sterilization.

The sterilization is usually executed in the daytime, so electric charge for the sterilization executed in the daytime is greater than that executed in the night.

However, since an operator is required to run the sterilizer, the sterilization cannot be constantly executed in the night in spite of low charge.

Thus, a fourth object of the present invention is to provide a small-sized steam sterilizer, e.g., a desk steam sterilizer, capable of reducing costs.

The inventors firstly studied to achieve the first object of the first to fourth objects, they found that the first object can be achieved by employing superheated steam, which is heated in a heat storage tank disclosed in Japanese Patent Gazette No. 2000-97498, as a heat source of a steam generator for generating saturated steam, without employing steam generated by a large boiler, then they reached a first basic structure of the present invention.

Namely, the saturated steam generator for generating saturated steam by heating water with superheated steam resulting from being superheated in a heat transmission tube inserted into a heat storage tank is characterized by, the provision of a saturated steam generator tank, wherein in the heat storage tank, disposed in a heat storage section composed by having a solid heat storage material and a liquid heat storage material filled therein are the heat transmission tube and a heater, which heats the solid heat storage material and the liquid heat storage material, and it being arranged that superheated steam resulting from passing through the heat transmission tube is used as a heat source to heat stored water so as to generate saturated steam.

In the first basic structure, by filling the solid heat storage material and the liquid heat storage material in the heat storage section of the heat storage tank with high density, heat capacity stored in the heat storage section and heat conductivity can be improved. Since sufficient heat capacity can be stored in the heat storage section by the heater, the heat stored in the heat storage materials is supplied to the heat transmission tube, and the water in the heat transmission tube can be immediately formed into the superheated steam even if the heater for heating the heat storage materials is out of operation.

Further, since the superheated steam generated in the heat storage tank is used as the heat source for heating the water stored in the saturated steam generator tank, sufficient temperature difference between the superheated steam and the saturated steam can be produced, and heat transmission area of the heater for heating the water stored in the saturated steam generator tank can be smaller than that in the case of using saturated steam as a heat source, so that the saturated steam generator can be small-sized, and the saturated steam can be generated in a short time from the out of operation state.

The inventors found that load of a large boiler can be reduced by employing said saturated steam generator, and they reached the second basic structure of the present invention.

Namely, the second basic structure is a steam sterilizer having a sterilizing chamber, in which an article to be sterilized is accommodated, and a saturated steam generator, which supplies saturated steam into the sterilizing chamber, wherein the saturated steam generator comprising: a heat storage tank including a heat storage section, in which a solid heat storage material and a liquid heat storage material are filled, and in which a heater for heating the solid heat storage material and the liquid heat storage material and a heat transmission tube for blowing off superheated steam generated by superheating water supplied are provided; a saturated steam generator tank, in which stored water is heated, by the superheated steam blown off from the heat transmission tube as a heat source, so as to generate saturated steam; and a steam supply tube supplying the saturated steam generated in the saturated steam generator tank into the sterilizing chamber.

In the saturated steam generator of the steam sterilizer of the second basic structure, by filling the solid heat storage material and the liquid heat storage material in the heat storage section of the heat storage tank with high density, heat capacity stored in the heat storage section and heat conductivity can be improved. Since sufficient heat capacity can be stored in the heat storage section by the heater, the heat stored in the heat storage materials is supplied to the heat transmission tube, and the water in the heat transmission tube can be immediately formed into the superheated steam even if the heater for heating the heat storage materials is out of operation.

Further, since the superheated steam generated in the heat storage tank is used as the heat source for heating the water stored in the saturated steam generator tank, sufficient temperature difference between the superheated steam and the saturated steam can be produced, and heat transmission area of the heater for heating the water stored in the saturated steam generator tank can be smaller than that in the case of using saturated steam as a heat source, so that the saturated steam generator can be small-sized, and the saturated steam can be generated in a short time from the out of operation state.

As described above, the steam sterilizer of the second basic structure has the saturated steam generator which is small-sized and capable of generating saturated steam in a short time from the out of operation state, so the steam sterilizer can be small-sized and capable of operating with independent cycles.

In the first and the second basic structures, if the solid heat storage material filled in the heat storage section includes solid heat storage grains having different diameters, each of the solid heat storage grains having short grain diameters is provided between the solid heat storage grains having large diameters and gaps between the heat storage grains are filled with the liquid heat storage material, density of the both heat storage materials in the heat storage section can be greater and heat capacity stored in the heat storage section can be greater, too.

Preferably, the solid heat storage material may include grains made of one or more selected from magnesia, magnetite, silica and alumina, and the liquid heat storage material may be a nitrate.

The heater for heating the solid heat storage material and the liquid heat storage material may be an electric heater so that heat can be stored in the heat storage materials by low cost midnight electric power, therefore clean and inexpensive saturated steam can be gained.

Further, if the saturated steam generator further comprise: a water supply tank for supplying water to the saturated steam generator tank; and a drain tube connecting the saturated steam generator tank to the water supply tank so as to use drain of the superheated steam, which is used in the saturated steam generator tank as the heat source, as a heat source for heating the water in the water supply tank, the heated water can be supplied to the saturated steam generator tank, so that further inexpensive saturated steam can be gained.

If the saturated steam generator tank comprises: an evaporation tank in which the stored water is heated and saturated steam is generated by a heater whose heat source is superheated steam supplied from the heat storage tank; and a level detection tank which is communicated to the evaporation tank and which includes means for detecting level of the water stored in the evaporation tank, the water level in the evaporation tank can be easily controlled.

If the saturated steam generator further comprises means for removing drain from saturated steam generated in the saturated steam generator tank, the saturated steam including no drain can be gained.

If a body proper of the sterilizing chamber includes: an inner cylinder in which the article to be sterilized is accommodated; an outer cylinder, which is provided outside of the inner cylinder; and a jacket which is provided between the inner cylinder and the outer cylinder and to which steam for heating the sterilizing chamber is supplied, and wherein the saturated steam generated in the saturated steam generator is directly supplied into the sterilizing chamber, different kinds of proper steam can be respectively supplied to the sterilizing chamber and the jacket according to purposes.

The inventors studied to achieve the third object of the present invention, they found that water is evaporated from the article and temperature of the article is fallen in a dry step for drying the article which has been wetted in a sterilization step, but temperature of the article can be risen without substantially wetting the article, in the dry step, by using the superheated steam instead of heated air, so that they reached a third basic structure.

Namely, the third basic structure is a steam sterilizer having a sterilizing chamber, which is provided in a body proper and in which an article to be sterilized is sterilized by saturated steam and the article, on which condensed water of the saturated steam is stuck, is dried, comprising: means for reducing pressure in the sterilizing chamber and evaporating the water stuck on the article; means for blowing the superheated steam into the sterilizing chamber, whose pressure has been reduced, so as to rise temperature of the article, whose temperature has been fallen by evaporating the water by pressure reduction; a control section alternately actuating the pressure reducing means and the blowing means so as to dry the article; and means for supplying the superheated steam, which has a heat storage tank including a heat storage section, in which a solid heat storage material and a liquid heat storage are filled, and in which a heater for heating the solid heat storage material and the liquid heat storage material and a heat transmission tube for blowing off superheated steam generated by superheating water supplied are provided.

Further, the method related to the third object is a steam sterilization method comprising the steps of: sterilizing an article to be sterilized, which is accommodated in a sterilizing chamber of a body proper of a sterilizer, by introducing saturated steam into the sterilizing chamber; reducing pressure in the sterilizing chamber so as to evaporate condensed water stuck on the article; blowing a heated fluid into the sterilizing chamber so as to rise temperature of the article, whose temperature has been fallen by evaporating the water stuck thereon, so as to rise the temperature of the article; and alternately repeating the reducing step and the blowing step so as to dry the article, wherein the heated fluid blown into the sterilizing chamber is superheated steam, and the superheated steam is supplied by using a heat storage tank having a heat storage section, in which a solid heat storage material and a liquid heat storage material are filled and in which a heater for heating the solid heat storage material and the liquid heat storage material and a heat transmission tube for blowing off superheated steam generated by superheating water supplied are provided.

In the third basic structure, heat capacity of the superheated steam supplied from the heat storage tank is much greater than that of heated air, and amount of water of the superheated steam is less than that of saturated steam of same pressure. As described as the third basic structure, in the dry step in which the article wetted by condensed water of the saturated steam is dried after the article is sterilized by the saturated steam, the temperature of the article can be risen without wetting the article by the superheated steam, even if the superheated steam is introduced into the sterilizing chamber so as to heat the article, from which water is evaporated and whose temperature is fallen under a pressure reducing atmosphere.

As described above, in the third basic structure, no heated air is introduced into the sterilizing chamber so as to heat the article whose temperature has fallen, so no heater for heating air is required.

In the third basic structure, if the body proper of the steam sterilizer is a single-wall pressure vessel, in which the sterilizing chamber is provided, the structure of the sterilizer can be simplified.

Further, the inventors studied to achieve the fourth object and found that costs of a small-sized steam sterilizer, e.g., a desk steam sterilizer, can be reduced by storing heat generated by midnight electric power in a heat storage tank even if the sterilizer is operated in the daytime, so that the inventors reached the fourth basic structure.

Namely, the fourth basic structure is a steam sterilizer comprising: a vessel, which is a pressure vessel and in which a sterilizing chamber for sterilizing an article to be sterilized accommodated therein and a water storing section are provided; and means for heating water stored in the water storing section to generate steam in the vessel, wherein the heating means includes: a heat storage tank, in which a heat storage section filled with a solid heat storage material and a liquid heat storage material, a heater for heating the heat storage section, and a heat transmission tube passing through the heat storage section so as to heat water in the heat storage section and blow off superheated steam are provided; and a superheated steam supply tube connected to the heat transmission tube so as to pass the superheated steam, which is generated in the heat storage section, through the water storing section.

In the fourth basic structure, preferably the solid heat storage material includes grains made of one or more selected from magnesia, magnetite, silica and alumina, and/or the liquid heat storage material is a nitrate.

BRIEF DESCRIPTION OF THE DRAWINGS

In the drawings,

FIG. 5 is a schematic view of an embodiment of a steam sterilizer of the present invention including the steam sterilizer shown in FIG. 1;

FIGS. 11 and 12 are partial schematic views of other embodiments of the steam sterilizer;

PREFERRED EMBODIMENTS OF THE INVENTION

Figure 1:
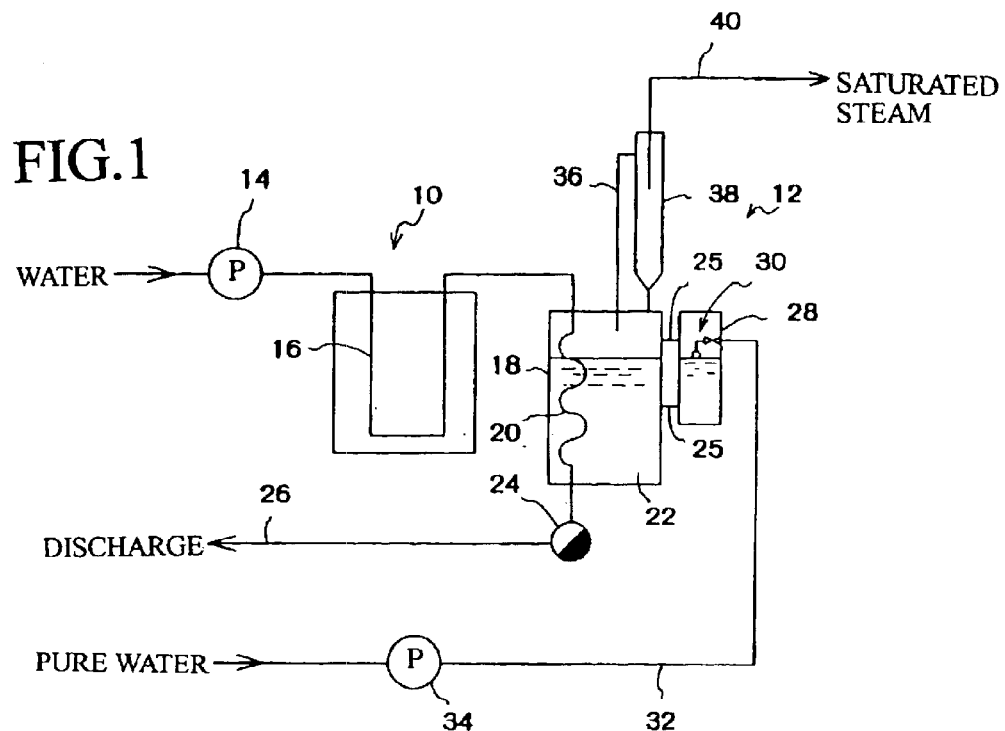
FIG. 1 is a schematic view of an embodiment of a saturated steam generator of the present invention.

A schematic view of a saturated steam generator related to the first basic structure is shown in FIG. 1. The saturated steam generator shown in FIG. 1 includes a heat storage tank 10 and a saturated steam generator tank 12.

A heat transmission tube 16 is provided in the heat starage tank 10, water is supplied to one end of the heat transmission tube 16 by a pump, and superheated steam is taken out from the other end thereof. The superheated steam, which is taken out from the other end of the heat transmission tube 16, is introduced to a heater 20, which is provided in an evaporation tank 18 constituting a saturated steam generator tank 12, then it heats water 22 stored in the evaporation tank 18 so as to generate superheated steam and condense the same.

Drain of the condensed superheated steam is separated from steam by a drain trap 24 and discharged from the system via a drain tube 26.

Preferably, the water supplied to the heat transmission tube 16 by the pump 14 is treated water, from which magnesium ions, calcium ions are removed by ion exchange resin, etc.

It is necessary to store a prescribed amount of the water 22 in the evaporating tank 18 in which saturated steam is generated, but a water surface of the water 22 in the evaporation tank 18 is unstable due to bubbles, so it is difficult to detect mean water level of the water 22 in the evaporation tank 18. Therefore, the saturated steam generator shown in FIG. 1 has a level detection tank 28 including level detecting means, which has communication tubes 25 and 25 communicated with a gaseous phase and a liquid phase so as to the water level of the water 22 stored in the evaporation tank 18. In the level detection tank 28, the unstable water surface of the water 22 in the evaporation tank 18 is standardized, so that the water level of the water 22 can be easily detected.

The level detecting means of the lever detection tank 28 shown in FIG. 1 is a float level meter 30; when the water level of the water 22 falls, a float of the level meter 30 moves downward, an inlet of a pure water supply tube 32 is opened, and a pump 34 connected to the pure water supply tube 32 is actuated to supply pure water to the level detection tank 28.

On the other hand, when the water level of the water 22 rises and reaches a prescribed level, the float of the level meter 30 moves upward and closes the inlet of the pure water supply tube 32, then the pump 34 is stopped.

Note that, if a position of the level detection tank 28 can be vertically changed, the water level of the water 22 in the evaporation tank 18 can be adjusted to a proper level at which proper heat exchangeability of the heater 20 can be gained.

The saturated steam (of the pure water) generated in the evaporation tank 18 is taken out from a steam tube 36 and supplied to a cyclone 38, which acts as means for removing drain in the saturated steam.

The saturated steam, from which the drain has been removed by the cyclone 38, is supplied to a user via a tube 40. No water conditioning agent is included in the steam, so it can be properly used for steam sterilization.

Note that, the pure water supplied into the level detection tank 28 may be produced by precise filtration and deionization treatment.

Figure 2:
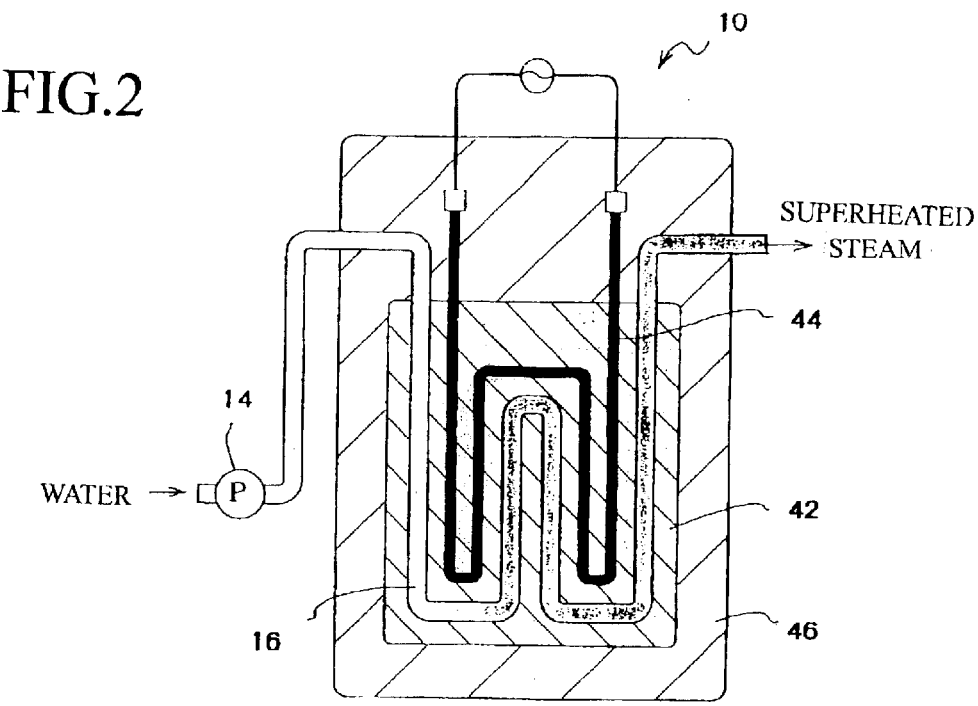
FIG. 2 is a sectional view of a heat storage tank 10 shown in FIG. 1.

A structure of the heat storage tank 10 of the saturated steam generator shown in FIG. 1 is shown in FIG. 2. The heat storage tank 10 shown in FIG. 2 has a heat storage section 42, in which a solid heat storage material and a liquid heat storage material are filled, and a heater 44 for heating the heat storage materials and the heat transmission tube 16, to which water is supplied by the pump 14, are also provided in said section. An outer circumferential face of the heat storage section 42 is covered with a heat insulating material 46 so as to prevent heat radiation from the heat storage section 42.

The solid heat storage material filled in the heat storage section 42 includes solid heat storage grains having different diameters, each of the solid heat storage grains having short grain diameters is provided between the solid heat storage grains having large diameters, and gaps between the heat storage grains are filled with the liquid heat storage material.

Figure 3A:
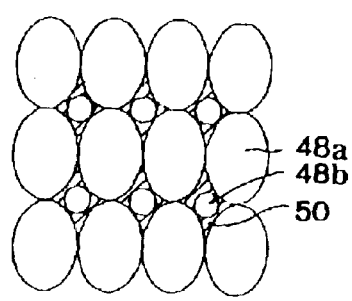
FIGS. 3A and 3B are explanation views of heat storage materials filled in a heat storage section 42.

The heat storage section 42 filled with the heat storage materials is shown in FIG. 3. In FIG. 3A, the solid heat storage material, which is constituted by solid heat storage grains 48a having large grain diameters and solid heat storage grains 48b having short grain diameters, and the liquid heat storage material 50 are filled, each of the solid heat storage grains 48b is provided between the solid heat storage grains 48a, and the gaps between the solid heat storage grains 48a and 48b are filled with the liquid heat storage material 50.

Figure 3B:
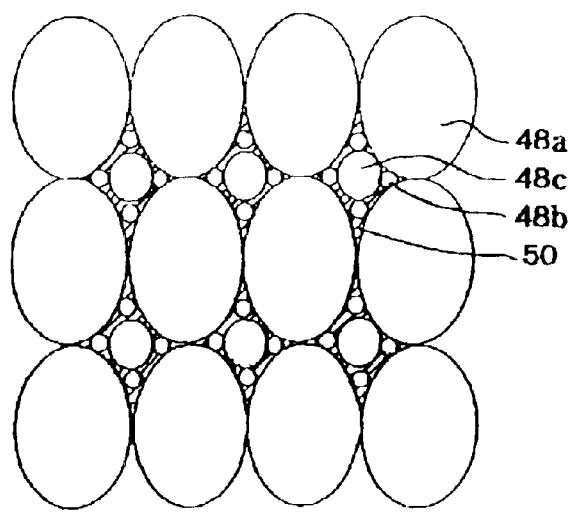

In FIG. 3B, three kinds of solid heat storage grains and the liquid heat storage material are filled in the heat storage section 42. The solid heat storage grains are the solid heat storage grains 48a having large grain diameters, the solid heat storage grains 48b having short grain diameters and solid heat storage grains 48c having medium grain diameters, which is shorter than that of the grains 48a and greater than that of the grains 48b; each of the solid heat storage grains 48c is provided between the solid heat storage grains 48a; and each of the solid heat storage grains 48b is provided between the solid heat storage grains 48a and 48c. Further, the gaps between the solid heat storage grains 48a, 48b and 48c are filled with the liquid heat storage material 50.

As shown in FIGS. 3A and 3B, in the heat storage section 42 in which the solid heat storage grains having short grain diameters are provided between the solid heat storage grains having large grain diameters and the gaps between the solid heat storage grains are filled with the liquid heat storage material; filling density of the solid heat storage grains having different grain diameters can be made higher than that of the solid heat storage grains having same grain diameters, so that storable heat capacity and heat conductivity to the heat transmission tube 12 can be improved.

Preferably, the solid heat storage material shown in FIGS. 3A and 3B includes the solid heat storage grains made of one or more selected from magnesia, magnetite, silica and alumina, and the liquid heat storage material is a nitrate. The nitrate is solidified at the room temperature; it is melted and formed into a liquid at temperature of 142° C. or more.

In the heat storage section 42 of the present embodiment, the solid heat storage material includes large magnesia grains whose grain diameters are 7–10 mm and small magnesia grains whose grain diameters are 1 mm or less, and total weight of the magnesia grains is 1800 kg; and the liquid heat storage material is the nitrate, and its weight is 370 kg. The heat storage materials in the heat storage section 42 is constituted by: 55% of the large magnesia grains; 25% of the small magnesia grains; and 20% of the nitrate.

The heater 44 whose electric power is 27 kW and the heat transmission tube 16 whose heat transmission area is 3.4 $m^2$ is provided in the heat storage section 42, and the heat storage section 42 is encased by the heat insulating material 46. The heat insulating material 46 is a fine porous material, which is mainly made of silicon oxide and titanium oxide and whose thickness is 50 mm. Sizes of the heat storage tank 10 are as follows: thickness 830 mm; width 1200 mm; height 1900 mm; and weight 3000 kg.

Electric power was applied to the electric heater 44 in the heat storage tank 10 for about 10 hours in the night, then water was continuously supplied to the heat transmission tube 16 in a state that water pressure of an outlet of the transmission tube 16 was 0.5 MPa, and temperature of steam and the heat storage materials were observed. The results are shown in FIG. 4.

Figure 4:
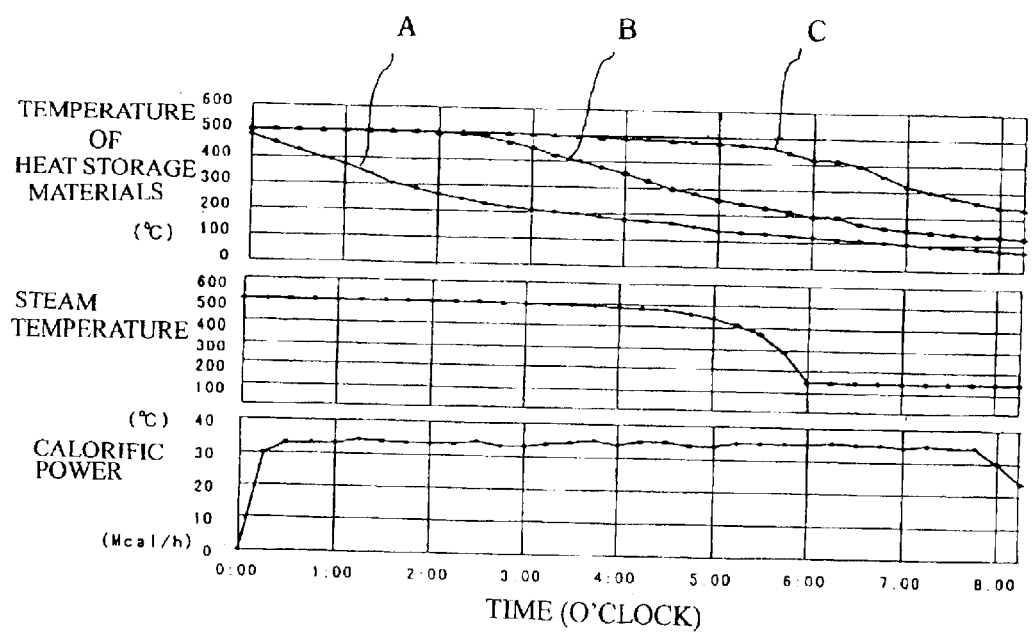
FIG. 4 is a graph of variation of output heat of the heat storage tank 10 with respect to time elapsed.

In FIG. 4, a curve "A" shows temperature of the heat storage materials near an inlet of the heat transmission tube 16; a curve "B" shows temperature of the heat storage materials near a mid part of the heat transmission tube 16; and a curve "C" shows temperature of the heat storage materials near the outlet of the heat transmission tube 16. The steam temperature is temperature of the steam blown out from the outlet of the heat transmission tube 16. Further, variation of the calorific power, which is calculated on the basis of the steam temperature at the outlet of the transmission tube 16 and amount of water supplied to the heat transmission tube 16, with respect to time elapsed is also shown in FIG. 4.

As clearly shown in FIG. 4, the heat storage materials was heated until high temperature of 500° C., and superheated steam of 500° C. was blown off from the heat transmission tube 16. The superheated steam could be continuously blown off for about four hours. Even if the temperature of the superheated steam blown was fallen to 500° C. or less, the superheated steam was still blown off; the superheated steam could be continuously blown off for eight hours or more. The calorific power was stable for about seven and half hours from the beginning.

This can be understood by the facts: the temperature of the heat storage materials near the inlet of the heat transmission tube 16 was fallen at the beginning; the temperature of the heat storage materials near the mid part of the heat transmission tube 16 was begun to fall when two and half hours elapsed; and the temperature of the heat storage materials near the outlet of the heat transmission tube 16 was begun to fall when five hours elapsed. By gradually changing points of taking out the heat from the heat transmission tube 16, the temperature and the calorific power of the superheated steam blown off from the heat transmission tube 16 can be stable.

By using the electric heater 44, the heat storage materials can be heated by clean electric energy; further, by using inexpensive midnight electric power, the superheated steam can be generated by clean and inexpensive energy.

In an ordinary heavy oil boiler capable of generating superheated steam for eight hours or more, an oil tank, an oil supply pipe, an air duct, an exhaust pipe, etc. must be required, so that the boiler must be large-sized. On the other hand, in the heat storage tank shown in FIG. 2, the electric heater 44 is used for heating the heat storage materials, so that no attached facilities, e.g., oil tank, is required and the heat storage tank can be small-sized.

It is theoretically possible to adjust humidity of the superheated steam blown off from the heat transmission tube 16 so as to produce saturated steam by adding water drops, but it is actually difficult to adjust the humidity, especially it is very difficult in the case of varying amount of use of saturated steam in a short time.

On the other hand, in the saturated steam generator shown in FIG. 1, since the superheated steam blown off from the outlet of the heat transmission tube 16 of the heat storage tank 10 is introduced to the heater 20 of the evaporation tank 18 which acts as the heat source for heating the pure water 22 in the evaporation tank 18 and generating saturated steam, the saturated steam can be stably supplied to an apparatus in which amount of use of the saturated steam varies in a short time.

A steam sterilizer, which is an example of the apparatus having the saturated steam generator shown in FIG. 1 and in which amount of use of the saturated steam varies in a short time, is shown in FIG. 5.

The steam sterilizer shown in FIG. 5 is an example of the second basic structure of the present invention, and a body proper 50 of the steam sterilizer includes: an inner cylinder 54 having a sterilizing chamber, in which articles to be sterilized will be accommodated; an outer cylinder 56 located outside of the inner cylinder 54; and a jacket 58 provided between the inner cylinder 54 and the outer cylinder 56.

In the steam sterilizer shown in FIG. 5, steam generated in a large boiler is introduced to the jacket 58 via a steam tube 62 having a control valve 60 so as to heat the inner cylinder 54 only. The steam heating the inner cylinder 54 is condensed and formed into drain, and the drain is discharged to outside of the system via a drain trap 66 of a discharge tube 64.

A tube 72 having a filter 68 and a control valve 70 is connected to the sterilizing chamber 52 so as to introduce air into the sterilizing chamber 52, and the supply tube 40 of the saturated steam generator shown in FIG. 1 is connected to the tube 72, whose connecting point is located between the control valve 70 and the sterilizing chamber 52; with this structure, the saturated steam (pure steam) can be directly supplied into the sterilizing chamber 52 by opening a control valve 74 of the supply tube 40.

Drain of the steam, which has been supplied into the sterilizing chamber 52 and has heated and sterilized the articles, is discharged via a discharge tube 76 and a drain trap 78, and the steam in the sterilizing chamber 52 is discharged via a control valve 80 which bypasses the drain trap 78.

When pressure in the sterilizing chamber 52 falls until reaching the atmospheric pressure, the control valve 80 is closed, a water ring vacuum pump 82 is actuated and a control valve 86 of a vacuum tube 84 is opened so as to produce a vacuum condition in the sterilizing chamber 52. The reason is to dry the articles, which have been wetted by condensed water of the pure steam while sterilizing.

When the pressure in the sterilizing chamber 52 is raised to the atmospheric pressure and the articles sterilized are taken out therefrom, the control valve 70 is opened so as to introduce clean air into the sterilizing chamber 52 via a filter 68.

Note that, a part of sealing water in the water ring vacuum pump 82 is lost by evaporation when the vacuum pump sucks the steam in the sterilizing chamber 52, but the loss of the sealing water can be supplemented via a tube 88.

Steps of the steam sterilization in the steam sterilizer shown in FIG. 5 will be explained with reference to FIG. 14, in which the variation of the inner pressure of the sterilizing chamber with respect to time elapsed is shown.

The steps of the steam sterilization are the conditioning (vacuum) step, the sterilization step, the discharge step, the dry step and the final step.

Firstly, the conditioning (vacuum) step is started after the sterilizing chamber 52, in which the articles to be sterilized have been accommodated, is air-tightly closed. In the conditioning (vacuum) step, the control valve 60 is opened so as to introduce steam generated in the large boiler is introduced to the jacket 58 and heat the sterilizing chamber 52, then the vacuum pump 82 is actuated and the control valve 86 is opened so as to discharge air from the sterilizing chamber 52 and produce the vacuum condition therein.

The pure steam, which has been generated in the evaporation tank 18 and taken out via the steam tube 36 and from which the drain has been removed by the cyclone 38, is supplied into the sterilizing chamber 52, by opening the control valve 74, so as to rise the inner pressure of the sterilizing chamber 52 and sterilize the articles therein.

After the control valve 80 is opened so as to discharge air in the sterilizing chamber 52 and return to the atmospheric pressure, the vacuum pump 82 is actuated and the control valve 86 is opened so as to produce the vacuum condition therein. Then, the conditioning step alternately repeats two actions: a vacuum supplying action, in which the pure steam is supplied into the vacuum sterilizing chamber 52; and a discharging action, in which the pure steam is discharged therefrom, the cycle of the vacuum supplying action—the discharging action is repeated a plurality of times. The conditioning (vacuum) step is executed so as to securely discharge air in the articles and rise inner temperature of the articles as well as surface temperature thereof when the steam is supplied into the sterilizing chamber 52 to heat the articles, as described later.

After the articles are fully heated in the conditioning (vacuum) step, the control valve 74 is opened to supply the saturated pure steam into the sterilizing chamber 52 until reaching prescribed pressure, then the pressure and temperature in the sterilizing chamber 52 are maintained for a prescribed time. With this action, bacilli stuck on the articles accommodated in the sterilizing chamber 52 can be sterilized.

Then, the pressurizing steam in the sterilizing chamber 52 is discharged by opening the control valve 80, and the dry step, in which the articles wetted in the sterilization step will be dried, is started.

In the dry step, the pressurizing steam has been discharged from the sterilizing chamber 52 and the pressure therein has been reduces to the atmospheric pressure, then the inner pressure of the sterilizing chamber 52 is further reduced to the vacuum condition by opening the control valve 86 (closing the control valve 80) and actuating the vacuum pump 82 so as to evaporate water stuck on the sterilized articles.

By evaporating water included in the articles, the temperature of the articles fall, thus the control valve 70 is opened to introduce heated clean air into the sterilizing chamber 52 and rise the inner pressure of the sterilizing chamber 52 to near the atmospheric pressure, so that the temperature of the articles are risen. Further, the vacuum condition is produced in the sterilizing chamber 52 again so as to dry the articles, then the heated clean air is introduced thereinto, the heating action and the pressure reducing action are alternately repeated a plurality of times so as to fully dry the articles. The reason of repeating the actions is that bacilli in the air stick onto and proliferate on the articles if the articles not sufficiently dried are taken out from the sterilizing chamber 52.

After the dry step is completed, clean air is introduced into the sterilizing chamber 52 by opening the control valve 70.

Note that, the steam is supplied to the jacket 58 during the steps, so that the sterilizing chamber 52 is always heated.

Figure 14:
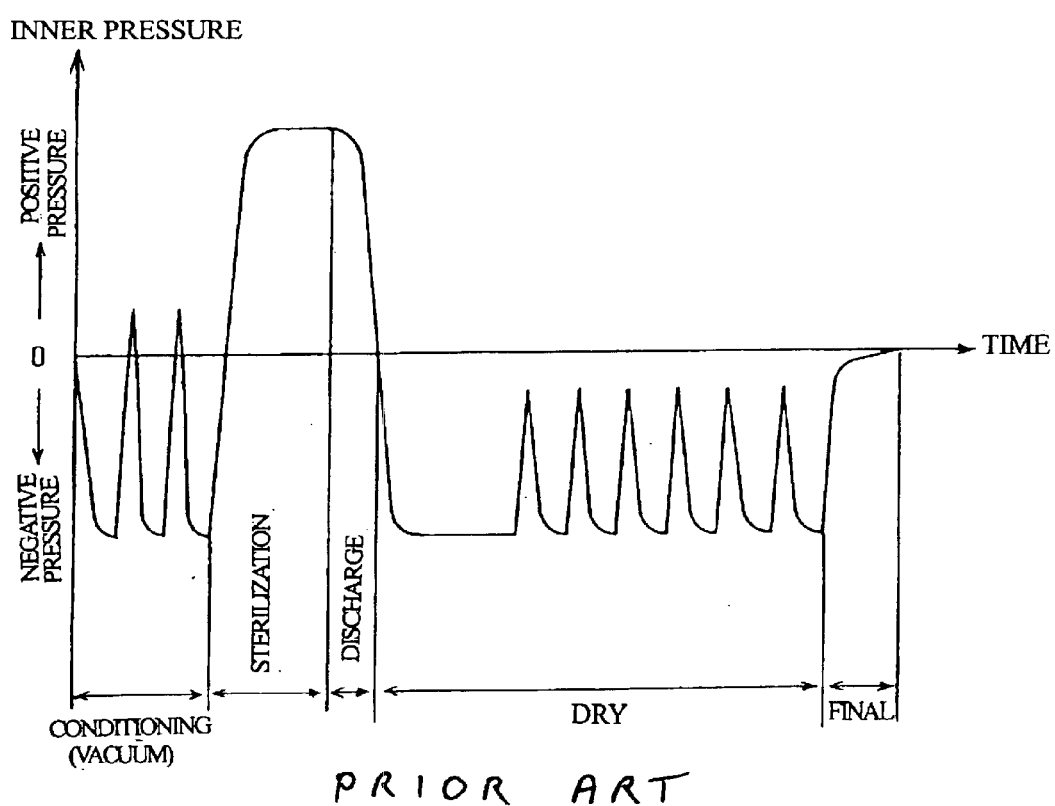
FIG. 14 is an explanation view of the conventional steam sterilization method executed in the sterilizer shown in FIG. 13.

As clearly shown in FIG. 14 in which the variation of the inner pressure in the sterilizing chamber, in the conditioning (vacuum) step and the sterilization step, the pure steam is intermittently supplied into the sterilizing chamber 52, the pure steam, which is generated by the saturated steam generator having the heat storage tank 10, is supplied without no problems.

Further, the saturated steam generator is small-sized, so it can be easily attached onto a rear face or a side face of the body proper 50 of the steam sterilizer.

The saturated steam generator shown in FIG. 1 can be easily applied to the conventional steam sterilizer, in which steam is supplied to the sterilizing chamber 52 from a large boiler, and pure steam can be supplied to the sterilizing chamber 52.

Figure 6:
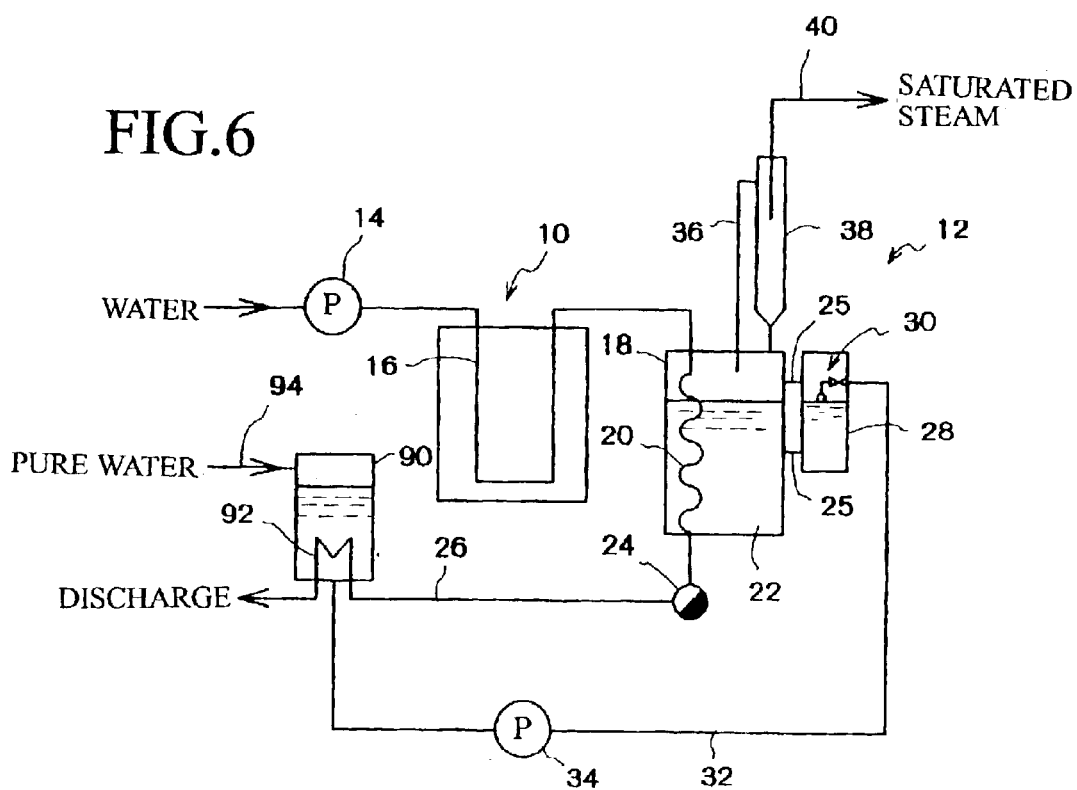
FIGS. 6, 7, 8 and 9 are schematic views of other embodiments of the steam sterilizer of the present invention.

In the saturated steam generators shown in FIGS. 1 and 5, the pure water is supplied to the level detection tank 28, which is communicated to the evaporation tank 18, by the pump 34; preferably, as shown in FIG. 6, preheated pure water is supplied to the level detection tank 28 so as to reduce a required calorific value for generating saturated steam in the evaporation tank 18.

In the saturated steam generator shown in FIG. 6, a heater 92 is provided in a water supply tank 90, which supplies pure water to the evaporation tank 18, so as to heat the water 22 stored in the evaporation tank 18; the drain, which is formed by condensing the saturated steam, is supplied to the heater via the drain trap 24 and the drain tube 26 so as to heat the pure water in the water supply tank 90. The heated pure water is supplied to the level detection tank 28 by the pump 34.

Figure 7:
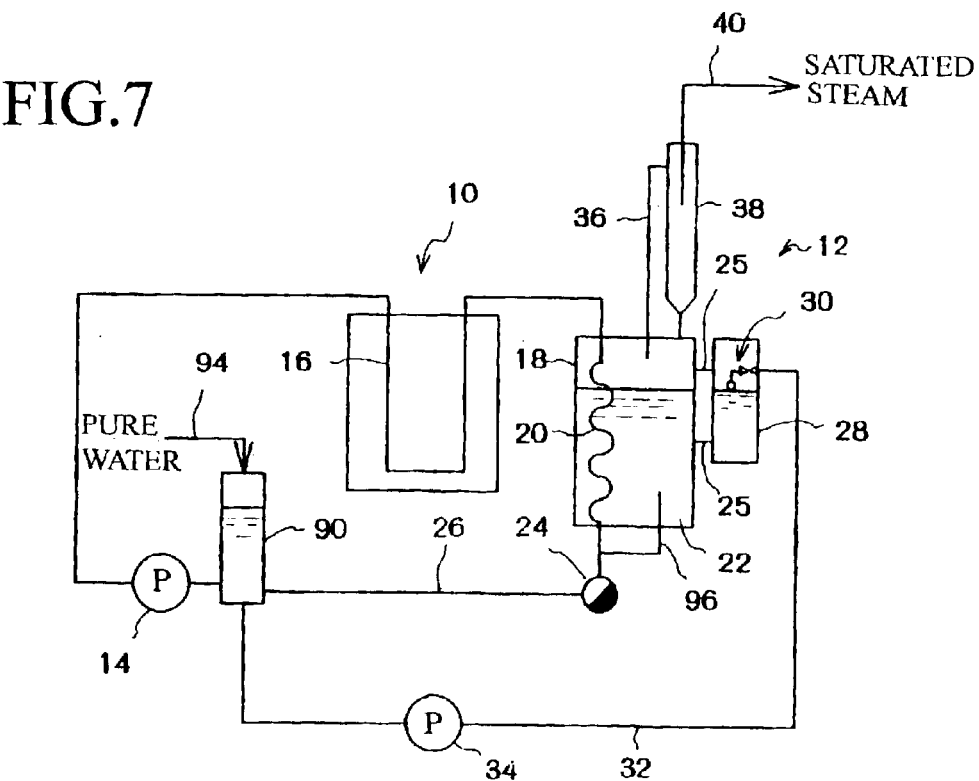

In FIGS. 1, 5 and 6, the water supplied to the heat transmission tube 16 of the heat storage tank 10 is different from the pure water supplied to the level detection tank 28; in FIG. 7, pure water is supplied to the heat transmission tube 16, namely the pure water can be supplied to the heat transmission tube 16 of the heat storage tank 10 and the level detection tank 28 from the same water supply tank 90.

In the case of supplying the pure water into the heat transmission tube 16 of the heat storage tank 10 and the level detection tank 28, a tube 96 for taking out a part of the drain and a part of the superheated steam is provided under the heater 20, and a part of the drain and a part of the superheated steam can be introduced into the stored water 22, so that thermal efficiency can be improved.

Further, the drain discharged to the drain tube 26 via the drain trap 24 can be returned to the water supply tank 90 to reuse and capable of heating the water therein. By supplying the heated pure water to the heat transmission tube 16 which has been heated to high temperature, heat shock caused by supplying cool pure water to the heat transmission tube 16 can be lightened.

Figure 8:
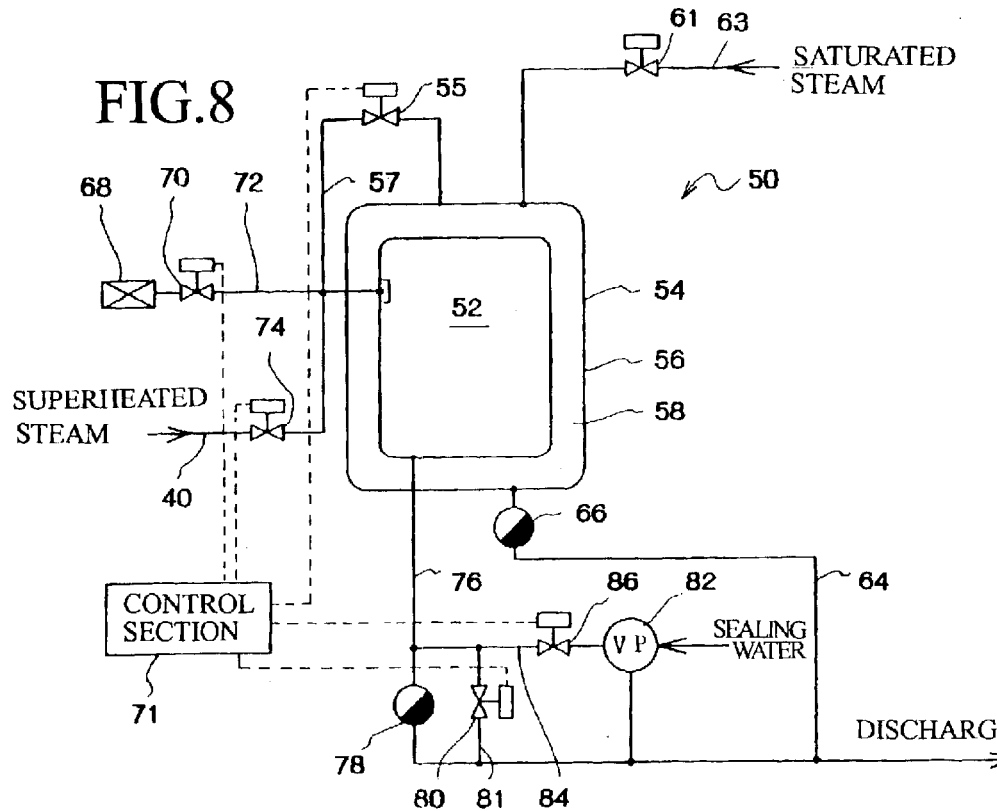

In the steam sterilizer shown in FIG. 5, the heated clean air is introduced into the sterilizing chamber 52 so as to heat and dry the articles sterilized; superheated steam may be used for drying the articles in the steam sterilizer as shown in FIG. 8. By using the superheated steam for drying the articles, a heater for heating air can be omitted and the steam sterilizer can be small-sized.

The steam sterilizer shown in FIG. 8 is an example of the third basic structure of the present invention, and the body proper 50 of the steam sterilizer includes: the inner cylinder 54 having the sterilizing chamber 52, in which the articles to be sterilized will be accommodated; the outer cylinder 56 located outside of the inner cylinder 54; and the jacket 58 provided between the inner cylinder 54 and the outer cylinder 56.

Saturated steam is introduced to the jacket 58 via a tube having a control valve 61, and the saturated steam, which has been introduced to the jacket 58, is introduced into the sterilizing chamber 52 via a tube 57 having a control valve 55.

The tube 72, in which the filter 68 is provided to one end and the control valve 70 is provided to a mid part, is connected to the sterilizing chamber 52 so as to introduce clean air, which has passed through the filter 68, into the sterilizing chamber 52. No means for heating air passing through the tube 72 is provided to the tube 72.

The tube 40 for introducing superheated steam is connected to the sterilizing chamber 52, and the control valve 74 is provided to a mid part of the tube 40.

A part of the saturated steam, which has been introduced to the jacket 58, is condensed and formed into condensed water by heat radiation from an outer face of the outer cylinder 56 and an inner face of the inner cylinder 54, and the condensed water is discharged via the drain trap 66 of the tube 64, whose one end is connected to the jacket 58.

A part of the saturated steam, which has been introduced to the sterilizing chamber 52, is condensed and formed into condensed water, and the condensed water is discharged via the drain trap 78 of the tube 76, whose one end is connected to the sterilizing chamber 52. The tube 84, in which the vacuum pump 82 is connected to one end and the control valve 84 is connected to a mid part, is connected to a connecting position of the tube 76, which is located between the sterilizing chamber 52 and the drain trap 78.

Note that, a tube 81 bypasses the train trap 78, and the control valve 80 is provided to a mid part of the tube 81.

The control valves 55, 61, 74, 80 and 88 are respectively opened and closed by a control section 71 so as to execute the steps of the sterilization (the action of the control section 71, which transmits signals for opening and closing the control valves 55, 61, 74, 80 and 88, will be omitted in the following description).

Firstly, the conditioning step is started after the sterilizing chamber 52, in which the articles to be sterilized have been accommodated, is air-tightly closed. The conditioning step alternately repeats two actions: a heating action for heating the articles accommodated in the sterilizing chamber 52 by opening the control valve 55 of the tube 57 so as to introduce the saturated steam, which has been introduced to the jacket 58, via the tube 63 and the control valve 61, thereinto; and a pressure reducing action for reducing the inner pressure of the sterilizing chamber 52 by actuating the vacuum pump 82 and opening the control valve 86 so as to discharge air and steam therefrom.

After the articles are fully heated in the conditioning step, the control valve 55 is opened to supply the saturated pure steam into the sterilizing chamber 52 until reaching prescribed pressure, then the pressure and temperature in the sterilizing chamber 52 are maintained for a prescribed time. With this action, bacilli stuck on the articles accommodated in the sterilizing chamber 52 can be sterilized.

Then, the pressurizing steam in the sterilizing chamber 52 is discharged by opening the control valve 80, and the dry step, in which the articles wetted in the sterilization step will be dried, is started.

In the dry step, the pressurizing steam has been discharged from the sterilizing chamber 52 and the pressure therein has been reduces to the atmospheric pressure, then the inner pressure of the sterilizing chamber 52 is further reduced to the vacuum condition by opening the control valve 86 (closing the control valve 80) and actuating the vacuum pump 82 so as to evaporate water stuck on the sterilized articles.

By evaporating water included in the articles, the temperature of the articles fall, thus the control valve 74 is opened to introduce superheated steam into the sterilizing chamber 52 via the tube 40 and rise the inner pressure of the sterilizing chamber 52 to near the atmospheric pressure, so that the temperature of the articles are risen.

Heat capacity of the superheated steam introduced into the sterilizing chamber 52 is greater than that of heated air; therefore, required volume of the superheated steam for heating the articles until reaching the prescribed temperature is less than that of the heated air.

Under the same pressure, amount of water per a unit volume in superheated steam is less than that in saturated steam; even if the superheated steam is introduced into the sterilizing chamber 52 to rise the temperature of the articles, whose temperature has been fallen by evaporation under the pressure reduction atmosphere, the superheated steam can rise the temperature of the articles without substantially wetting them.

The inner pressure of the sterilizing chamber 52 is reduced again so as to dry the articles, whose temperature has been risen by introducing the superheated air into the sterilizing chamber 52.

In the dry step, the, heating action, in which the superheated steam is introduced into the sterilizing chamber so as to heat the articles, and the pressure reducing action, in which water is evaporated from the articles by reducing the inner pressure of the sterilizing chamber 52, are alternately repeated so as to fully dry the articles.

After the dry step is completed, clean air is introduced into the sterilizing chamber 52 by opening the control valve 70.

Note that, the steam is supplied to the jacket 58 during the steps, so that the sterilizing chamber 52 is always heated.

The superheated steam, which is introduced into the sterilizing chamber 52 via the tube 40, is supplied form the heat storage tank 10 shown in FIG. 2. The heat storage tank 10 shown in FIG. 2 has been explained, therefore explanation will be omitted hereinafter.

In the steam sterilizer shown in FIG. 8, the body proper 50 has a double-wall structure including the inner cylinder 54 and the outer cylinder 56.

But, in the dry step of the steam sterilizer shown in FIG. 8, the superheated steam is used instead of heated air, so the tube 72 for heating air to be introduced into the sterilizing chamber 52 need not be wound on the outer face of the outer cylinder 56.

Figure 9:
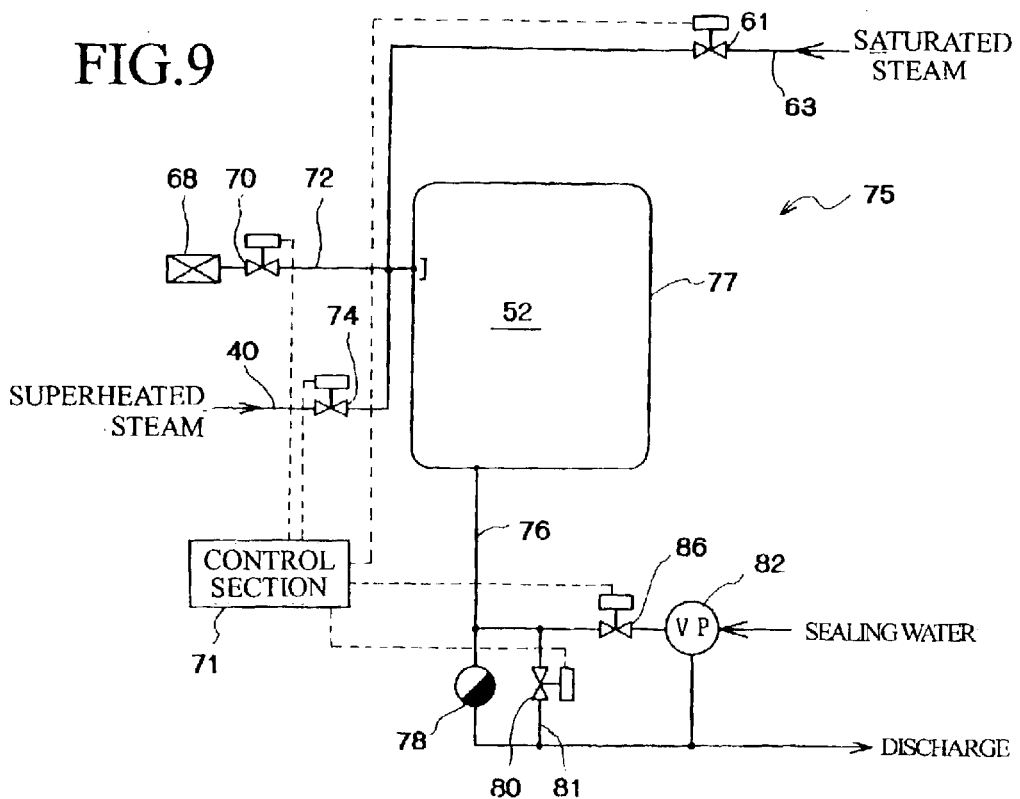

Therefore, as clearly shown in FIG. 9, a body proper 75 may be a single-wall pressure vessel 77 having the sterilizing chamber. A structure of the pressure vessel 77 is simpler than that of the double-wall pressure vessel shown in FIG. 5.

Since the pressure vessel 77 shown in FIG. 9 has no jacket, saturated steam introduced by the tube 63 is directly supplied to the sterilizing chamber 52.

The sterilizing chamber 52 is heated by the saturated steam introduced by the tube 63 or superheated steam introduced by the tube 40; preferably, heat radiation from the pressure vessel 77 is reduced by a lagging material.

Note that, in FIG. 9, the structural elements equal to those of the steam sterilizer shown in FIG. 5 are assigned the same symbols of FIG. 1, and detail explanation will be omitted.

Figure 10:
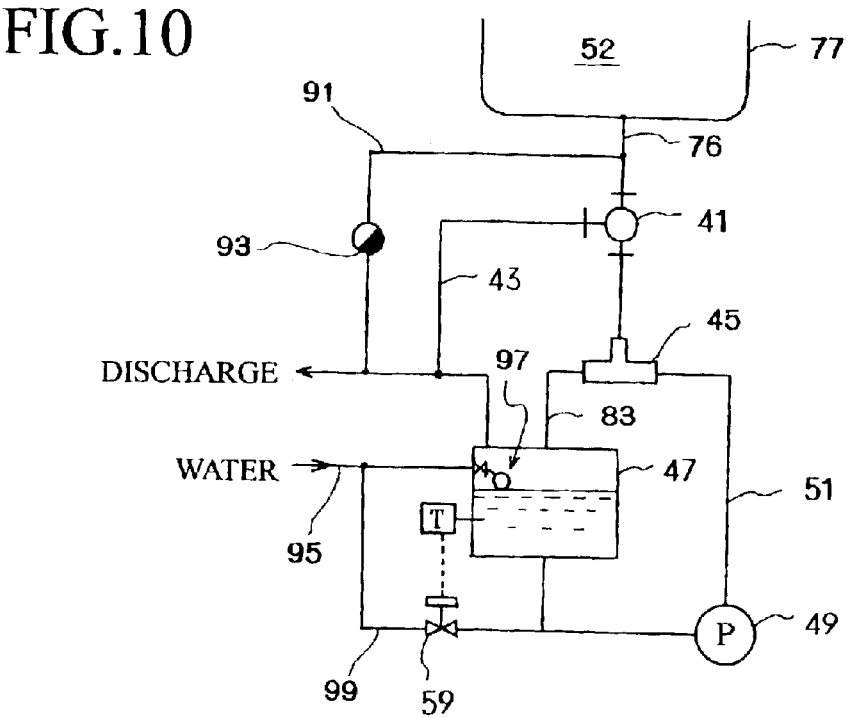
FIG. 10 is a partial schematic view of other embodiment of the steam sterilizer.

In the steam sterilizers shown in FIGS. 5 and 9, the water ring vacuum pump 82 is used as the means for reducing the inner pressure of the sterilizing chamber 52; in FIG. 10, a water ejector unit is used as the reducing means.

In the water ejector unit, a three-way valve 41 is provided to the tube 76 connected to the sterilizing chamber 52, an air sucking port of a water ejector 45 is connected to one valve seat of the three-way valve 41, and a tube 43 for releasing inner pressure of the sterilizing chamber 52 is connected to another valve seat of the three-way valve 41.

Water to be jetted is supplied from a water tank 47 to the water ejector 45, by a pump 49, via a tube 51; the water jetted from the water ejector 45 is returned to the water tank 47 via a tube 83.

By contact with the steam in the sterilizing chamber 52, the water jetted from the water ejector 45 evaporates, thus water level of the water tank 47 is monitored by a float-type level meter 97 and the water level is maintained by supplementing water via a tube 95.

The stored water in the water tank 47 is jetted from the water ejector 45 and circulated, so temperature of the stored water is gradually risen. On the other hand, degree of vacuum in the sterilizing chamber 52 is made lower with raising the temperature of the water jetted from the water ejector 45. Therefore, the temperature of the water in the water tank 47 is measured by a thermo sensor "T"; when the temperature of the water exceeds prescribed temperature, the control valve 59 of a tube 99, which is branched from a tube 95, is opened so as to supply water into the water tank 47 and adjust the temperature of the water stored therein.

Note that, condensed water, which is formed by condensing the steam supplied in the sterilizing chamber 52, is discharged via a drain trap 93, which is provided to a tube 91 branched from the tube 76.

In the case of reducing the inner pressure of the sterilizing chamber 52 by the water ejector unit shown in FIG. 10, the sterilizing chamber 52 is connected to the tube 43 by the three-way valve 41 so as to release the inner pressure of the sterilizing chamber 52.

When the inner pressure of the sterilizing chamber 52 reaches the atmospheric pressure, the sterilizing chamber 52 is connected to the water ejector 45 by the three-way valve 41 and water is supplied to the water ejector 45 by the pump 49.

After that, when the inner pressure of the sterilizing chamber 52 reaches prescribed degree of vacuum, the three-way valve 41 comes into a neutral state, the sterilizing chamber 52 is included in a closed system and the pump 49 is stopped.

FIG. 10 shows the water ejector unit, but a air ejector unit, which jets air instead of water, may be employed.

In the air ejector unit, the degree of vacuum depends on air temperature; preferably, means for adjusting the air temperature is provided to the air ejector unit.

In the above described embodiments, the superheated steam is used in the dry step, which is executed after the sterilization, but the superheated steam may be used in the conditioning step so as to rise the temperature of the articles to be sterilized.

In the above described embodiments, the heat storage section 42 is filled with the solid heat storage grains having different grain diameters, and each of the small solid heat storage grains is provided between the large solid heat storage grains and the gaps between the heat storage grains are filled with the liquid heat storage material; in the case that amount of generating the saturated steam is small and the heat storing capacity of the heat storage tank 10 is also small, the heat storage section 42 may be filled with solid heat storage grains having substantially same diameters and the liquid heat storage material.

In the embodiments shown in FIGS. 1, 5, 6 and 7, the pure water is supplied to the level detection tank 28; if steam of pure water is not required, treated water, from which magnesium ions, calcium ions, etc. are removed by ion exchange resin, can be used so as to prevent deposition of scales and reduction of heat conductivity.

The saturated steam generator shown in FIG. 1 may be used for supplying the saturated steam to a dry cleaning finisher other than the steam sterilizer. Further, the saturated steam generator shown in FIG. 1 can be used for not only the apparatus, in which amount of saturated steam used is varied, but also an apparatus, in which fixed amount of saturated steam is used for a prescribed time.

Note that, the electric heater 44 is used for heating the heat storage materials in the heat storage tank 10, but other heating means, e.g., high temperature gas exhausted from a plant, steam generated by a boiler, may be used as the heater.

The steam sterilizers shown in FIGS. 5, 8 and 9 are large steam sterilizers installed in hospitals; a small-sized or a desk steam sterilizer, which is preferably used in a clinic, is shown in FIG. 11.

The steam sterilizer 330 shown in FIG. 11 comprises: a vessel section 331, which is a pressure vessel including a sterilizing chamber 332; a water storing section 334 provided a lower part of the vessel section 331; and heating means 339 for heating the water stored in the water storing section 334. The heating means 339 includes a heater 336 provided in the water storing section 334 and the heat storage tank 10 capable of heating the heater 336.

Note that, the heat storage tank 10 is separated from a body proper 330a, in which the sterilizing chamber 32 is provided, and its structure is equal to that of the heat storage tank 10 shown in FIGS. 2–4, so explanation will be omitted.

A water supply tank 364 is connected to the heat storage tank 10, the water supplied from the water supply tank 364 is superheated in the heat storage tank 10 and supplied to a steam tube 336 as superheated steam. The superheated steam, which has exchanged heat with the water in the water storing section, is condensed and returned to the water supply tank 364 so as to reuse.

The vessel section 331 is the pressure vessel, which can be air-tightly closed and which includes a plate 333 on which articles (not shown) to be sterilized will be mounted.

A part of an inner space of the vessel section 331 under the plate 333 is formed into a tank or the water storing section 334. In the sterilization step, the water in the water storing section 334 is heated so as to fill the vessel 331 with steam.

Water stored in a water tank 342 is supplied to the water storing section 334 via a water supply tube 340, in which a three-way control valve 344 is provided to a mid part. One of ports of the three-way control valve 344 is connected to a condensing pipe 348 in the water tank 342 via a tube 345.

Note that, the water tank 342 has a pipe 361 used as a discharge pipe and as a level meter.

A tube 352, in which an air pump 347 is provided to a front end and a filter 349, a control valve 350 and a heater 347 are provided to mid parts, is connected to the sterilizing chamber 332 of the vessel 331 so as to suck air.

Air in the sterilizing chamber 332 is discharged via an exhaust tube 354. An electromagnetic valve 355 is connected to the exhaust tube 354; exhausted steam is introduced to a condensing pipe 356 in the water tank 342 via the electromagnetic valve 355.

The exhaust tube 354 is also connected to a pressure gauge 359, an exhaust pressure switch 357 and a safety valve 358 provided in the water tank 342.

The steam tube 336, which is provided in the water storing section 334 so as to superheat the water, is a metallic pipe, through which the superheated steam generated in the heat storage tank 10 is passed. The metallic pipe is dipped in the water of the water storing section 334, so that the heat of the superheated steam is conducted to the water and the water can be heated.

Preferably, the steam tube 336 is wound like a coil or formed into a wave shape so as to make heat transmission area broader.

The heat transmission tube 16 is provided in the heat storage tank 10, and a water supply pipe 365 extended from the water supply tank 364 is connected to one end of the heat transmission tube 16. The water in the water supply tank 364 is supplied to the heat transmission tube 16 in the heat storage tank 10 by a pump 366; the superheated steam, which has been generated by the heat storage materials in the heat storage tank 360, is taken out from the other end of the heat transmission tube 16.

A tube 368, which is extended to the water storing section 334, is connected to the other end of the heat transmission tube 16. The tube 368 is connected to one end of the steam tube 336 in the water storing section 334 so as to supply superheated steam into the water storing section 334.

A tube 369, which is extended to the water supply tank 364, is connected to the other end of the steam tube 336 in the water storing section 334. The tube 369 returns condensed water, which is formed by heat-exchanging in the water storing section 334, to the water supply tank 364. With this structure, the water in the water supply tank 364 is circulated via the heat storage tank 10 and the seam tube 336.

Preferably, treated water, from which magnesium ions, calcium ions are removed by ion exchange resin, etc. is used as the water, which is stored in the water supply tank 364 and superheated in the heat storage tank 10, so as to prevent deposition of scales in the heat transmission tube 16 and the steam tube 336.

As shown in FIG. 4, in the heat storage tank 10, the heat storage materials were heated to high temperature of 500° C. by the electric heater after midnight electric power was applied to the electric heater in the heat storage tank 10 for 10 hours; the temperature of the steam blown off from the heat transmission tube 16 was also 500° C.

Further, the superheated steam of 500° C. could be continuously blown off for four hours. Even if the temperature of the superheated steam fell less than 500° C., the superheated steam could be still blown off; the superheated steam could be blown off for eight hours or more. Calorific power outputted was stable for about seven and half hours from the beginning.

By employing the heat storage tank 10, the heat storage materials can be heated by inexpensive midnight electric power, so that clean and inexpensive superheated steam can be generated In the steam sterilizer shown in FIG. 11 including the heat storage tank 10, the heat previously stored by inexpensive midnight electric power is used for generating the superheated steam instead of an electric heater, so that costs of the steam sterilizer can be reduced.

Figure 12:
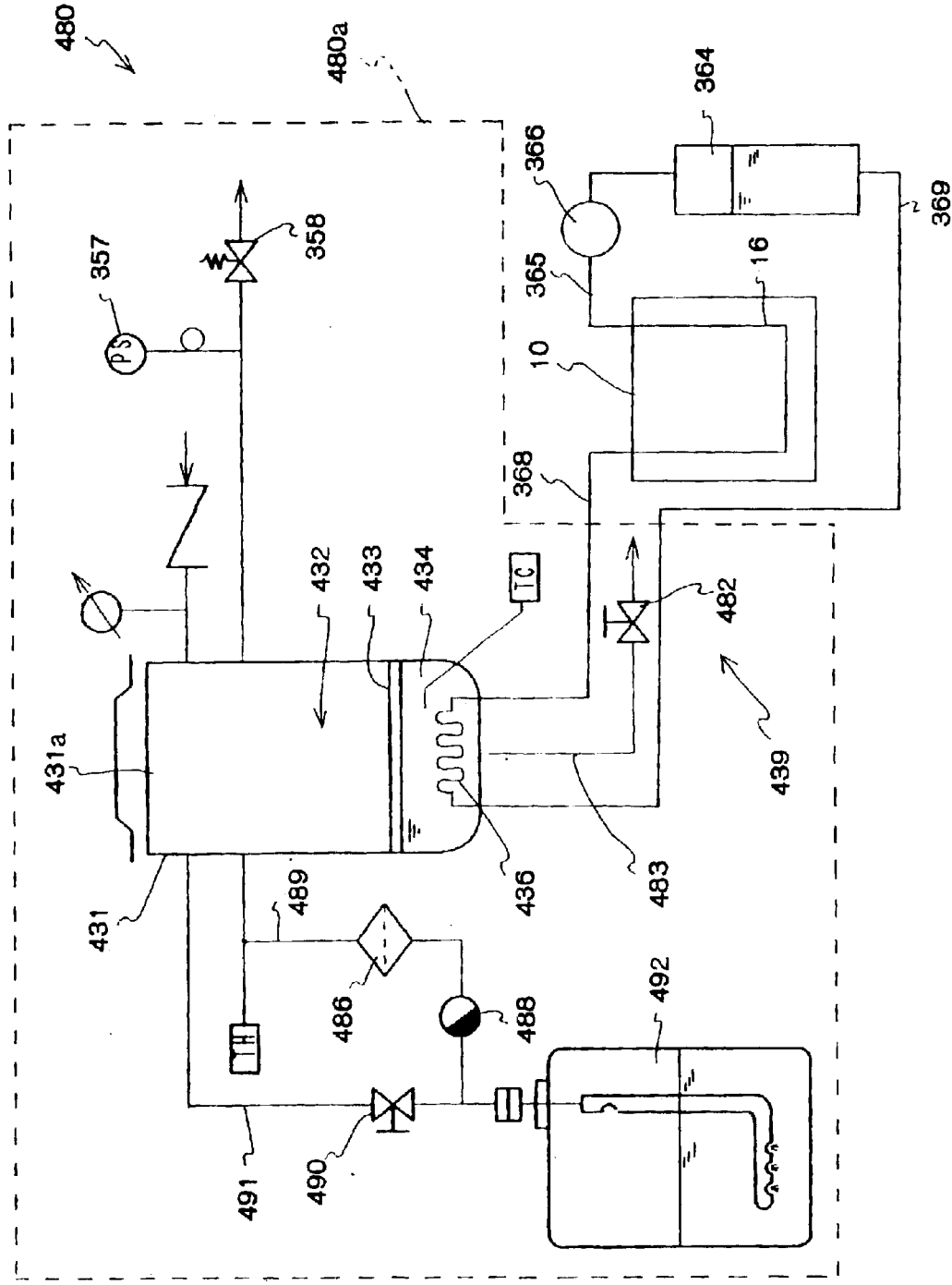
Figure 13:
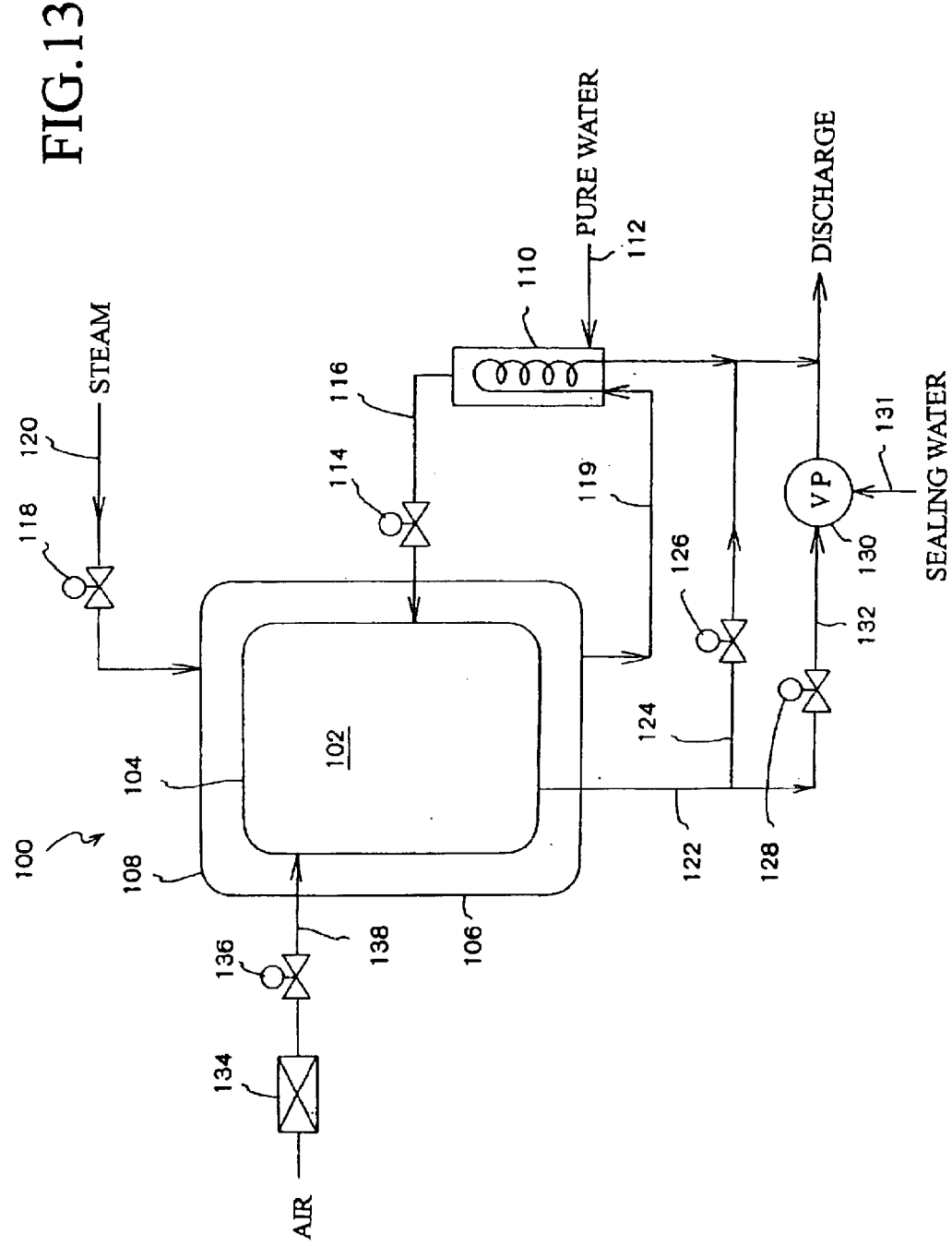
FIG. 13 is a schematic view of the conventional steam sterilizer.
Figure 15:
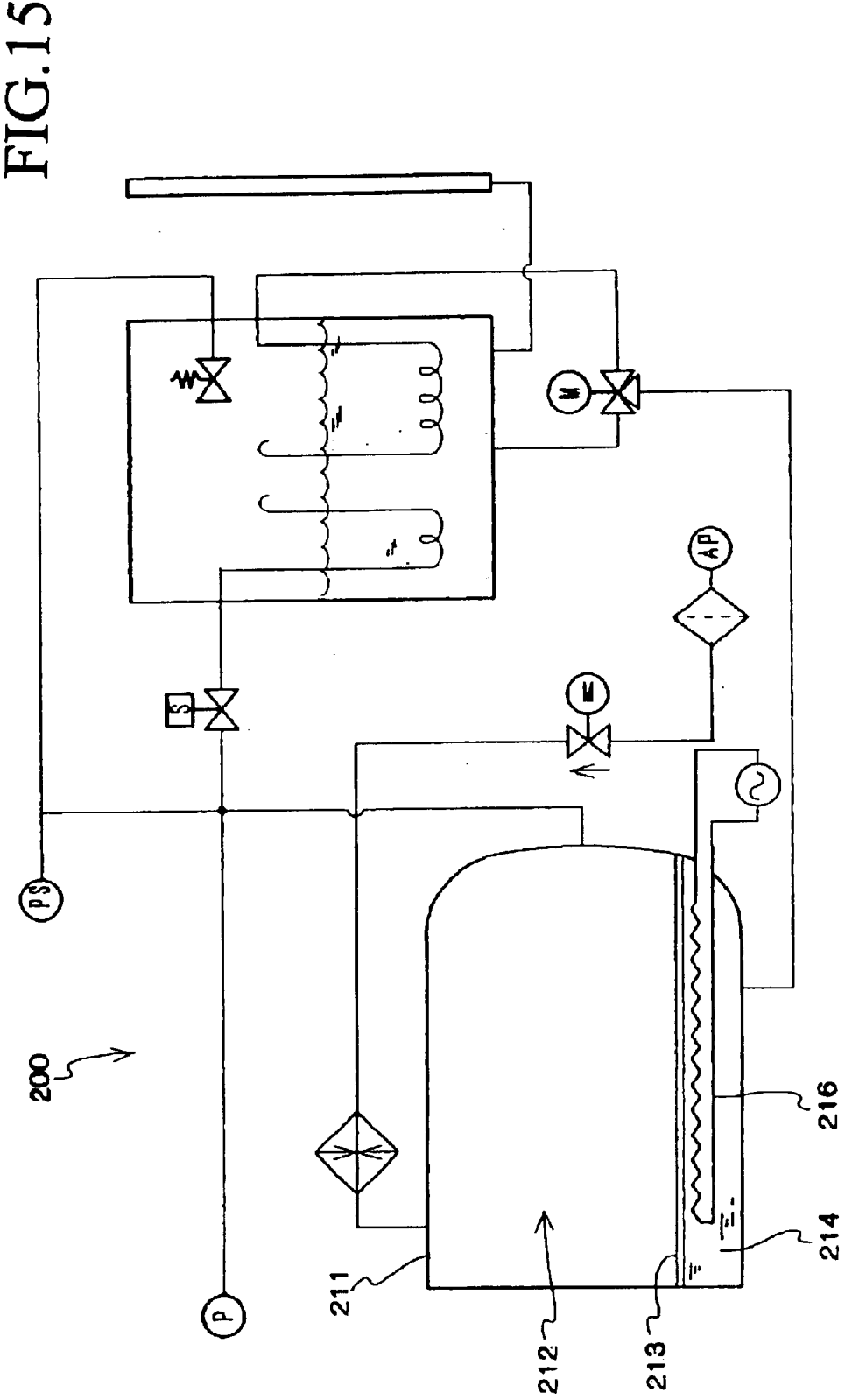
FIG. 15 is a schematic view of another conventional steam sterilizer.

The steam sterilizer 330 shown in FIG. 11 is a horizontal type steam sterilizer; a vertical type steam sterilizer is shown in FIG. 12.

Unlike the horizontal type steam sterilizer 330 shown in FIG. 11; in a steam sterilizer 480 shown in FIG. 12, a vessel section 431 is vertically installed, and an opening section 431a of the vessel section 431 is headed upward. The structural elements constituting the steam sterilizer 330 shown in FIG. 11 are assigned the same symbols and explanation will be omitted.

The vertical type steam sterilizer 480 comprises: the vessel section 431, which is a pressure vessel including a sterilizing chamber 432; a water storing section 434, which is a lower part of the vessel section 431; and heating means 439 for heating the water stored in the water storing section 434.

In some cases, a water tank for supplementing water is connected to the water storing section 434, but it is omitted in the present embodiment. A plate 433, on which articles to be sterilized will be mounted, is provided in the vessel section 431.

The water in the water storing section 434 is discharged by a discharge valve 482 provided to a tube 483.

A tube 489, to which a filter 486 and a drain trap 488 are provided, is connected to the sterilizing chamber 432, and an exhaust bottle 492 is connected thereto via an exhaust tube 491, to which an exhaust valve 490 is provided.

In the vertical type steam sterilizer 480 too, the water stored in the water storing section 434 is heated by the heating means 439.

The heating means 439 comprises: the heat storage tank 10 including the heat storage section, which is filled with the solid heat storage material and the liquid heat storage material and in which the electric heater for heating the heat storage materials and the heat transmission tube 16 to which water is supplied by the pump 366; and a steam supply tube 436 for introducing superheated steam, which has been generated in the heat storage tank 10, into the water storing section 434 so as to heat the water therein.

Note that, the heat storage tank 10 is separated from a body proper 480a including the sterilizing chamber 432.

The superheated steam passing through the steam supply tube 436, which has exchanged heat with the water in the water storing section 434, is condensed, and the condensed water is returned to the water supply tank 364. The water in the water supply tank 364 is supplied to the heat storage tank 10 again so as to generate superheated steam.

In the vertical type steam sterilizer 480 shown in FIG. 12, the superheated steam, which is generated by the heat stored by inexpensive midnight electric power, is used for generating the steam used in the steam sterilizer 480. Therefore, costs of the steam sterilizer 480 shown in FIG. 12 can be reduced.

FIELD OF INDUSTRIAL APPLICABILITY

The saturated steam generator of the first basic structure has the heat source for heating stored water and generating saturated steam, and it can be small-sized. Therefore, saturated steam can be separately generated from a large boiler, so apparatuses, which consume a large amount of steam exceeding capacity of the large boiler, can be added.

The steam sterilizer of the second basic structure has the small-sized saturated steam generator including the heat source for heating stored water and generating saturated steam; therefore, saturated steam can be separately generated from a large boiler, so apparatuses, which consume a large amount of steam exceeding capacity of the large boiler, can be added.

In the third basic structure of the present invention, the articles, which have been wetted in the sterilization step, can be dried, in the dry step, without substantially using heated air. Therefore, no heater, which heats air so as to dry the wet articles, is required. Further, heat capacity of the superheated steam is greater than heated air, so a required amount of superheated steam can be less than that of heated air. Unlike the conventional steam sterilizer in which the articles wetted in the sterilization step are dried by heated air in the dry step, the structure of the steam sterilizer of the present invention can be simplified.

By employing the fourth basic structure, in a small-sized or a desk steam sterilizer too, the superheated steam, which is generated by the heat stored by inexpensive midnight electric power, is used for generating the steam used in the steam sterilizer; therefore, costs of the small-sized steam sterilizer can be reduced.

What is claimed is:

1. A saturated steam generator for generating saturated steam from water heated with superheated steam, comprising:
   a heat transmission tube for generating superheated steam;
   a heat storage tank having a heat storage section containing a solid heat storage material, a liquid heat storage material, and a heater which heats the solid heat storage material and the liquid heat storage material so as to generate superheated system in the heat transmission tube passing through the heat storage section;
   a saturated steam generating tank storing pure water; and
   wherein a portion of superheated steam is directly blown into the pure water stored in said saturated steam generating tank, as a heat source to heat the stored pure water, and generates saturated steam in said saturated steam generating tank.

2. The saturated steam generator according to claim 1, wherein said solid heat storage material in said heat storage section includes particles of solid heat storage material having grains of different diameters, such that solid heat storage particles having small diameters are provided between solid heat storage particles having large diameters, and gaps between heat storage particles are filled with said liquid heat storage material.

3. The saturated steam generator according to claim 1, wherein said solid heat storage material comprises particles made of at least one substance selected from the group consisting of: magnesia, magnetite, silica and alumina.

4. The saturated steam generator according to claim 1, wherein said liquid heat storage material is a nitrate.

5. The saturated steam generator according to claim 1, wherein said heater is an electric heater.

6. The saturated steam generator according to claim 1, further comprising means for removing liquid condensate from saturated steam generated in said saturated steam generator tank.

7. The saturated steam generator according to claim 1, wherein said saturated steam generator tank comprises:
   an evaporation tank in which the stored water is heated and saturated steam is generated by a heater having superheated steam supplied from said heat storage tank as its heat source; and
   a level detection tank which is in fluid communication with said evaporation tank and which includes means for detecting a level of the water stored in said evaporation tank.

8. The saturated steam generator according to claim 1, further comprising:
   a water supply tank for supplying water to said saturated steam generator tank; and
   a drain tube connecting said saturated steam generator tank to said water supply tank for utilizing liquid condensate obtained from the superheated steam used as the heat source in said saturated steam generator tank, as a heat source for heating the water in said water supply tank.

9. A steam sterilizer, comprising:
   a sterilizing chamber, in which an article to be sterilized is placed; and
   a saturated steam generator, which supplies saturated steam into said sterilizing chamber;
   wherein said saturated steam generator comprises:
      a heat storage tank, including a heat storage section, containing a solid heat storage material and a liquid heat storage material,
      a heater, in said heat storage tank, for heating the solid heat storage material and the liquid heat storage material, and
      a heat transmission tube for blowing off superheated steam generated by superheating water;
   a saturated steam generator tank, in which stored pure water is heated, by directly blowing off a portion of the superheated steam from the heat transmission tube, in which the superheated steam is generated by heating pure water supplied therein, so as to generate saturated steam; and
   a steam supply tube, for supplying the saturated steam generated in said saturated steam generator tank into the sterilizing chamber.

10. The steam sterilizer according to claim 9, wherein said solid heat storage material in said heat storage section includes particles of solid heat storage material having grains of different diameters, such that solid heat storage particles having small diameters are provided between solid heat storage particles having large diameters, and gaps between heat storage particles are filled with said liquid heat storage material.

11. The steam sterilizer according to claim 9, wherein said solid heat storage material comprises particles made of at least one substance selected from the group consisting of: magnesia, magnetite, silica and alumina.

12. The steam sterilizer according to claim 9, wherein said liquid heat storage material is a nitrate.

13. The steam sterilizer according to claim 9, wherein a body of said sterilizing chamber comprises:
   an inner cylinder, in which an article to be sterilized is placed;
   an outer cylinder, outside of the inner cylinder; and
   a jacket, between the inner cylinder and the outer cylinder, to which steam for heating said sterilizing chamber is supplied, and wherein the saturated steam generated in said saturated steam generator is directly supplied into said sterilizing chamber.

14. The steam sterilizer according to claim 9, wherein the heater for heating the solid heat storage material and the liquid heat storage material constituting the heat storage section of said saturated steam generator is an electric heater.

15. The steam sterilizer according to claim 9, further comprising means for removing liquid condensate from saturated steam generated in said saturated steam generator tank.

16. The steam sterilizer according to claim 9, wherein said saturated steam generator tank comprises:
   an evaporation tank, in which the stored water is heated and saturated steam is generated by a heater utilizing superheated steam supplied from said heat storage tank as a heat source; and
   a level detection tank, which is in communication with said evaporation tank, and which includes means for detecting a level of the water stored in said evaporation tank.

17. The steam sterilizer according to claim 9, further comprising:
   a water supply tank, for supplying water to said saturated steam generator tank; and
   a drain tube, connecting said saturated steam generator tank to said water supply tank, for utilizing liquid condensate obtained from the superheated steam, which is used in said saturated steam generator tank, as a heat source for heating the water in said water supply tank.

18. The steam sterilizer according to claim 9, wherein the water stored in said saturated steam generator tank is pure water.

19. A steam sterilizer comprising:

a vessel, which is a pressure vessel, having a sterilizing chamber for sterilizing an article to be sterilized which is placed therein;

a water storing section; and heating means for heating water stored in the water storing section to generate steam in the vessel, wherein said heating means comprises:

a heat storage tank, having a heat storage section, filled with a solid heat storage material and a liquid heat storage material, a heater for heating said heat storage section, and a heat transmission tube passing through said heat storage section for heating water in said heat storage section and for blowing off superheated steam; and a superheated steam supply tube, connected to said heat transmission tube so as to pass the superheated steam, which is generated in said heat storage section, through said water storing section.

20. The steam sterilizer according to claim 19, wherein said solid beat storage material in said heat storage section includes particles of solid heat storage material having grains of different diameters, diameters, and gaps between heat storage particles are filled with said liquid heat storage material.

21. The steam sterilizer according to claim 19, wherein said solid heat storage material comprises particles made of at least one substance selected from the group consisting of: magnesia, magnetite, silica and alumina.

22. The steam sterilizer according to claim 19, wherein said liquid heat storage material is a nitrate.

* * * * *